(12) United States Patent
Ouyang et al.

(10) Patent No.: US 10,441,134 B2
(45) Date of Patent: Oct. 15, 2019

(54) METHOD AND APPARATUS FOR HYSTEROSCOPY AND ENDOMETRIAL BIOPSY

(71) Applicant: CooperSurgical, Inc., Trumbull, CT (US)

(72) Inventors: Xiaolong Ouyang, Palo Alto, CA (US); Paul D. Indman, San Jose, CA (US); Robert K. Deckman, San Bruno, CA (US); Shih-Ping Wang, Los Altos, CA (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 15/868,148

(22) Filed: Jan. 11, 2018

(65) Prior Publication Data
US 2018/0132701 A1 May 17, 2018

Related U.S. Application Data

(63) Continuation of application No. 14/115,318, filed as application No. PCT/US2012/034698 on Apr. 23, 2012.
(Continued)

(51) Int. Cl.
*A61B 1/00* (2006.01)
*A61B 10/02* (2006.01)
(Continued)

(52) U.S. Cl.
CPC ........ *A61B 1/00066* (2013.01); *A61B 1/0005* (2013.01); *A61B 1/00034* (2013.01);
(Continued)

(58) Field of Classification Search
CPC ..... A61B 10/04; A61B 34/25; A61B 1/00066; A61B 1/045; A61B 1/00128; A61B 1/05;
(Continued)

(56) References Cited

U.S. PATENT DOCUMENTS 4,137,920 A * 2/1979 Bonnet ............ A61B 17/32002
600/105
4,201,199 A 5/1980 Smith
(Continued)

FOREIGN PATENT DOCUMENTS

CN 2565407 8/2003
CN 2638669 9/2004
(Continued)

OTHER PUBLICATIONS

U.S. Appl. No. 12/911,297, filed Oct. 25, 2010, Ouyang.
(Continued)

*Primary Examiner* — Rene T Towa
(74) *Attorney, Agent, or Firm* — Fish & Richardson P.C.

(57) ABSTRACT

Methods and devices are described for performing a combined hysteroscopy and endometrial sampling. Techniques for improving visual images include forward facing fluid ports for clearing tissue debris and LED positioning and design. Manufacturability is improved through separately formed tip and shaft pieces. User interface features are described including user-friendly handle-mounted buttons as well the use of an interactive integrated touch screen display. The handle and display can be mated to a docking station for storage and recharging batteries.

30 Claims, 32 Drawing Sheets

Related U.S. Application Data

(60) Provisional application No. 61/482,200, filed on May 3, 2011, provisional application No. 61/482,309, filed on May 4, 2011, provisional application No. 61/485,601, filed on May 12, 2011, provisional application No. 61/490,029, filed on May 25, 2011, provisional application No. 61/494,400, filed on Jun. 7, 2011, provisional application No. 61/506,074, filed on Jul. 9, 2011, provisional application No. 61/515,092, filed on Aug. 4, 2011, provisional application No. 61/539,736, filed on Sep. 27, 2011, provisional application No. 61/544,280, filed on Oct. 7, 2011, provisional application No. 61/550,391, filed on Oct. 22, 2011, provisional application No. 61/555,470, filed on Nov. 3, 2011, provisional application No. 61/556,167, filed on Nov. 4, 2011, provisional application No. 61/570,816, filed on Dec. 14, 2011, provisional application No. 61/599,981, filed on Feb. 17, 2012, provisional application No. 61/600,593, filed on Feb. 18, 2012, provisional application No. 61/611,182, filed on Mar. 15, 2012, provisional application No. 61/623,376, filed on Apr. 12, 2012.

(51) Int. Cl.
| | | |
|---|---|---|
| *A61B 10/04* | (2006.01) | |
| *A61B 1/303* | (2006.01) | |
| *A61B 1/015* | (2006.01) | |
| *A61B 1/018* | (2006.01) | |
| *A61B 1/05* | (2006.01) | |
| *A61B 1/06* | (2006.01) | |
| *A61B 1/12* | (2006.01) | |
| *A61B 1/045* | (2006.01) | |
| *A61B 17/00* | (2006.01) | |
| *A61B 90/30* | (2016.01) | |
| *A61B 34/00* | (2016.01) | |
| *A61B 90/00* | (2016.01) | |

(52) U.S. Cl.
CPC ...... *A61B 1/00039* (2013.01); *A61B 1/00052* (2013.01); *A61B 1/00087* (2013.01); *A61B 1/00091* (2013.01); *A61B 1/00094* (2013.01); *A61B 1/00101* (2013.01); *A61B 1/00103* (2013.01); *A61B 1/00105* (2013.01); *A61B 1/00124* (2013.01); *A61B 1/00128* (2013.01); *A61B 1/00179* (2013.01); *A61B 1/015* (2013.01); *A61B 1/018* (2013.01); *A61B 1/045* (2013.01); *A61B 1/05* (2013.01); *A61B 1/053* (2013.01); *A61B 1/0607* (2013.01); *A61B 1/0676* (2013.01); *A61B 1/0684* (2013.01); *A61B 1/126* (2013.01); *A61B 1/303* (2013.01); *A61B 10/0275* (2013.01); *A61B 10/0291* (2013.01); *A61B 10/04* (2013.01); *A61B 1/00016* (2013.01); *A61B 1/00108* (2013.01); *A61B 34/25* (2016.02); *A61B 90/361* (2016.02); *A61B 2017/00221* (2013.01); *A61B 2090/309* (2016.02); *A61B 2090/372* (2016.02); *A61M 2210/1433* (2013.01)

(58) Field of Classification Search
CPC . A61B 1/00179; A61B 1/00039; A61B 1/126; A61B 1/0684; A61B 1/0676; A61B 1/0607; A61B 1/053; A61B 1/018; A61B 1/00034; A61B 1/00124; A61B 1/00103; A61B 1/00105; A61B 1/00101; A61B 1/00094; A61B 1/00091; A61B 1/00087; A61B 1/00052; A61B 1/0005; A61B 1/015; A61B 1/303; A61B 10/0291; A61B 10/0275; A61B 2090/309; A61B 2090/372; A61B 90/361; A61B 2017/00221; A61B 1/00016
See application file for complete search history.

(56) References Cited

U.S. PATENT DOCUMENTS

| | | | |
|---|---|---|---|
| 4,441,509 A | | 4/1984 | Kotsifas et al. |
| 4,475,539 A | | 10/1984 | Konomura |
| 4,836,189 A | | 6/1989 | Alfred et al. |
| 4,867,138 A | * | 9/1989 | Kubota ............ A61B 1/00098 |
| | | | 348/65 |
| 5,483,951 A | | 1/1996 | Frassica et al. |
| 5,484,422 A | | 1/1996 | Sloane et al. |
| 5,498,230 A | | 3/1996 | Adair |
| 5,506,912 A | | 4/1996 | Nagasaki et al. |
| 5,527,262 A | | 6/1996 | Monroe et al. |
| 5,591,119 A | | 1/1997 | Adair |
| 5,609,561 A | | 3/1997 | Uehara et al. |
| 5,637,074 A | | 6/1997 | Andino et al. |
| 5,662,586 A | | 9/1997 | Monroe et al. |
| 5,666,965 A | | 9/1997 | Bales et al. |
| 5,734,418 A | | 3/1998 | Danna |
| 5,751,341 A | | 5/1998 | Chaleki et al. |
| 5,823,940 A | | 10/1998 | Newman |
| 5,860,953 A | | 1/1999 | Snoke et al. |
| 5,873,816 A | | 2/1999 | Kagawa et al. |
| 5,879,289 A | | 3/1999 | Yarush et al. |
| 5,885,214 A | | 3/1999 | Monroe et al. |
| 5,902,230 A | | 5/1999 | Takahashi et al. |
| 5,929,901 A | | 7/1999 | Adair et al. |
| 5,986,693 A | | 11/1999 | Adair et al. |
| 5,993,378 A | | 11/1999 | Lemelson |
| 6,043,839 A | | 3/2000 | Adair et al. |
| 6,066,089 A | | 5/2000 | Costello et al. |
| 6,095,970 A | | 8/2000 | Hidaka et al. |
| 6,102,920 A | | 8/2000 | Sullivan et al. |
| 6,106,457 A | | 8/2000 | Perkins et al. |
| 6,203,493 B1 | | 3/2001 | Ben-Haim |
| 6,211,904 B1 | | 4/2001 | Adair et al. |
| 6,221,007 B1 | | 4/2001 | Green |
| 6,275,855 B1 | | 8/2001 | Johnson |
| 6,310,642 B1 | | 10/2001 | Adair et al. |
| 6,315,712 B1 | | 11/2001 | Rovegno |
| 6,348,035 B1 | | 2/2002 | Takami |
| 6,387,043 B1 | | 5/2002 | Yoon |
| 6,419,626 B1 | | 7/2002 | Yoon |
| 6,428,470 B1 | | 8/2002 | Thompson |
| 6,468,265 B1 | | 10/2002 | Evans et al. |
| 6,478,730 B1 | | 11/2002 | Bala et al. |
| 6,554,765 B1 | | 4/2003 | Yarush et al. |
| 6,593,587 B2 | | 7/2003 | Pease |
| 6,652,453 B2 | | 11/2003 | Smith et al. |
| 6,709,408 B2 | | 3/2004 | Fisher |
| 6,717,166 B2 | | 4/2004 | Pease |
| 6,858,857 B2 | | 2/2005 | Pease et al. |
| 6,858,858 B2 | | 2/2005 | Pease |
| 6,923,757 B2 | | 8/2005 | Abe et al. |
| 6,929,600 B2 | | 8/2005 | Hill |
| 6,979,290 B2 | | 12/2005 | Mourlas et al. |
| 6,982,740 B2 | | 1/2006 | Adair et al. |
| 7,030,904 B2 | | 4/2006 | Adair et al. |
| 7,033,314 B2 | | 4/2006 | Kamrava et al. |
| 7,041,050 B1 | * | 5/2006 | Ronald .......... A61B 17/320016 |
| | | | 600/104 |
| 7,074,182 B2 | | 7/2006 | Rovegno |
| 7,081,097 B2 | | 7/2006 | Martone et al. |
| 7,099,078 B2 | | 8/2006 | Spencer |
| 7,144,250 B2 | | 12/2006 | Fischer et al. |
| 7,214,183 B2 | | 5/2007 | Miyake |
| 7,365,768 B1 | | 4/2008 | Ono et al. |
| 7,384,308 B2 | | 6/2008 | Boehnlein et al. |
| 7,431,619 B2 | | 10/2008 | Boehnlein et al. |
| 7,445,596 B2 | | 11/2008 | Kucklick et al. |
| 7,500,947 B2 | | 3/2009 | Kucklick et al. |

(56) References Cited

U.S. PATENT DOCUMENTS

| | | |
|---|---|---|
| 7,520,854 B2 | 4/2009 | Sato |
| 7,530,946 B2 | 5/2009 | Hartwick |
| 7,581,988 B2 | 9/2009 | Boehnlein et al. |
| 7,584,534 B2 | 9/2009 | Pease et al. |
| 7,758,495 B2 | 7/2010 | Pease et al. |
| 7,783,133 B2 | 8/2010 | Dunki-Jacobs et al. |
| 7,794,409 B2 | 9/2010 | Damarati |
| 7,846,107 B2 | 12/2010 | Hoffman et al. |
| 7,850,601 B2 | 12/2010 | Uchimura et al. |
| 7,927,272 B2 | 4/2011 | Bayer et al. |
| 7,946,981 B1 | 5/2011 | Cubb |
| 7,959,561 B2 | 6/2011 | Akui et al. |
| 7,976,459 B2 | 7/2011 | Laser |
| 7,979,689 B2 | 7/2011 | Watt et al. |
| 8,004,560 B2 | 8/2011 | Sato et al. |
| 8,007,433 B2 | 8/2011 | Iketani |
| 8,022,979 B2 | 9/2011 | Miyamoto et al. |
| 8,025,670 B2 | 9/2011 | Sharp et al. |
| 8,033,993 B2 | 10/2011 | Amano et al. |
| 8,133,169 B2 | 3/2012 | Nagase et al. |
| 8,142,346 B2 | 3/2012 | Shoroji et al. |
| 8,144,191 B2 | 3/2012 | Kawanishi et al. |
| 8,157,726 B2 | 4/2012 | Melder |
| 8,177,710 B1 | 5/2012 | Hosaka et al. |
| 8,182,416 B1 | 5/2012 | Hosaka et al. |
| 8,189,043 B2 | 5/2012 | Schneider et al. |
| 8,218,074 B2 | 7/2012 | Pease et al. |
| 8,317,689 B1 | 11/2012 | Remijan et al. |
| 8,356,527 B2 | 1/2013 | Hudson |
| 8,382,665 B1 | 2/2013 | Fam |
| 8,403,831 B2 | 3/2013 | Kishioka |
| 8,416,291 B2 | 4/2013 | Carrey et al. |
| 8,453,639 B2 | 6/2013 | Kim et al. |
| 8,460,182 B2 | 6/2013 | Ouyang et al. |
| 8,535,219 B2 | 9/2013 | Smith et al. |
| 8,556,801 B2 | 10/2013 | Liu |
| 8,574,151 B2 | 11/2013 | Mitsuhashi |
| 8,581,971 B2 | 11/2013 | Miyamoto et al. |
| 8,591,401 B2 | 11/2013 | Miyayashiki et al. |
| 8,597,179 B2 | 12/2013 | Kokubo |
| 8,638,361 B2 | 1/2014 | Tanabe et al. |
| 8,641,605 B2 | 2/2014 | Shoroji et al. |
| 8,656,697 B2 | 2/2014 | Zubiate et al. |
| 8,872,906 B2 | 10/2014 | Bayer et al. |
| 9,622,646 B2 | 4/2017 | Ouyang |
| 2002/0077550 A1 | 6/2002 | Rabiner et al. |
| 2003/0040659 A1 | 2/2003 | Kazakevish |
| 2003/0195390 A1 | 10/2003 | Graumann |
| 2004/0054254 A1 | 3/2004 | Miyake |
| 2004/0122327 A1 | 6/2004 | Belson et al. |
| 2004/0210161 A1 | 10/2004 | Burdorff et al. |
| 2004/0220478 A1 | 11/2004 | Wallace et al. |
| 2005/0010081 A1 | 1/2005 | Dogushi et al. |
| 2005/0075538 A1 | 4/2005 | Banik et al. |
| 2005/0085690 A1 | 4/2005 | Tien |
| 2005/0136372 A1 | 6/2005 | Fischer et al. |
| 2006/0004258 A1 | 1/2006 | Sun et al. |
| 2006/0058703 A1 | 3/2006 | Huenerbein |
| 2006/0103729 A1* | 5/2006 | Burns .................. H04N 5/232 348/207.1 |
| 2006/0106281 A1 | 5/2006 | Boulais et al. |
| 2006/0155168 A1 | 7/2006 | Pease |
| 2006/0184187 A1 | 8/2006 | Surti |
| 2006/0258955 A1 | 11/2006 | Hoffman et al. |
| 2007/0030344 A1 | 2/2007 | Miyamoto et al. |
| 2007/0033626 A1 | 2/2007 | Yang et al. |
| 2007/0038020 A1 | 2/2007 | Tien |
| 2007/0129604 A1 | 6/2007 | Hatcher et al. |
| 2007/0167681 A1 | 7/2007 | Gill et al. |
| 2007/0185379 A1 | 8/2007 | Newman et al. |
| 2007/0225556 A1 | 9/2007 | Ortiz et al. |
| 2007/0225561 A1 | 9/2007 | Watanabe et al. |
| 2007/0249904 A1 | 10/2007 | Amano et al. |
| 2007/0265492 A1 | 11/2007 | Sonnenschein et al. |
| 2008/0042861 A1 | 2/2008 | Dacquay et al. |
| 2008/0045791 A1 | 2/2008 | Gal et al. |
| 2008/0046293 A1* | 2/2008 | Yamada ................ G06Q 50/24 705/3 |
| 2008/0051628 A1 | 2/2008 | Pecherer et al. |
| 2008/0058591 A1 | 3/2008 | Saadat et al. |
| 2008/0058595 A1 | 3/2008 | Snoke et al. |
| 2008/0076966 A1* | 3/2008 | Isaacson ................ A61B 1/303 600/106 |
| 2008/0086028 A1* | 4/2008 | Matsui ................ A61B 1/0005 600/109 |
| 2008/0097469 A1 | 4/2008 | Gruber et al. |
| 2008/0097470 A1 | 4/2008 | Gruber et al. |
| 2008/0108869 A1 | 5/2008 | Sanders et al. |
| 2008/0132763 A1 | 6/2008 | Isaacson |
| 2008/0195128 A1 | 8/2008 | Orbay et al. |
| 2008/0200758 A1 | 8/2008 | Orbay et al. |
| 2008/0243031 A1 | 10/2008 | Seibel et al. |
| 2009/0026888 A1 | 1/2009 | Melville |
| 2009/0030276 A1 | 1/2009 | Saadat et al. |
| 2009/0036742 A1 | 2/2009 | Watanabe |
| 2009/0082695 A1 | 3/2009 | Whitehead |
| 2009/0105538 A1 | 4/2009 | Van Dam et al. |
| 2009/0112058 A1 | 4/2009 | Kagawa |
| 2009/0118575 A1 | 5/2009 | Ichikawa et al. |
| 2009/0118580 A1 | 5/2009 | Sun et al. |
| 2009/0167849 A1 | 7/2009 | Niida |
| 2009/0196459 A1 | 8/2009 | Watt et al. |
| 2009/0221873 A1 | 9/2009 | McGrath |
| 2009/0225159 A1 | 9/2009 | Schneider et al. |
| 2009/0231419 A1 | 9/2009 | Bayer |
| 2009/0312607 A1 | 12/2009 | Sunagawa et al. |
| 2009/0318758 A1 | 12/2009 | Farr et al. |
| 2010/0022824 A1 | 1/2010 | Cybulski |
| 2010/0030020 A1 | 2/2010 | Sanders et al. |
| 2010/0033563 A1 | 2/2010 | Boehnlein et al. |
| 2010/0033986 A1 | 2/2010 | Schober et al. |
| 2010/0095969 A1 | 4/2010 | Schwartz et al. |
| 2010/0121139 A1 | 5/2010 | Ouyang et al. |
| 2010/0121142 A1 | 5/2010 | Ouyang et al. |
| 2010/0121155 A1 | 5/2010 | Ouyang et al. |
| 2010/0125164 A1* | 5/2010 | LaBombard ....... A61B 1/00087 600/104 |
| 2010/0128116 A1 | 5/2010 | Sato et al. |
| 2010/0185052 A1 | 7/2010 | Chang |
| 2010/0191050 A1 | 7/2010 | Zwolinski |
| 2010/0238278 A1 | 9/2010 | Rovegno |
| 2010/0262000 A1 | 10/2010 | Wallace et al. |
| 2010/0284580 A1* | 11/2010 | OuYang ................ G06T 7/0014 382/128 |
| 2010/0286477 A1 | 11/2010 | Ouyang et al. |
| 2011/0009694 A1 | 1/2011 | Schultz et al. |
| 2011/0034773 A1 | 2/2011 | Ishigami et al. |
| 2011/0090331 A1 | 4/2011 | Draper |
| 2011/0092842 A1 | 4/2011 | Decaria et al. |
| 2011/0112360 A1 | 5/2011 | Swann et al. |
| 2011/0112361 A1 | 5/2011 | Ishigami et al. |
| 2011/0130627 A1 | 6/2011 | McGrail et al. |
| 2011/0130632 A1 | 6/2011 | McGrail et al. |
| 2011/0137127 A1 | 6/2011 | Schwartz et al. |
| 2011/0152878 A1 | 6/2011 | Trusty et al. |
| 2011/0160537 A1 | 6/2011 | Chen |
| 2011/0187824 A1 | 8/2011 | Hori |
| 2011/0201884 A1 | 8/2011 | Kishioka |
| 2011/0218457 A1 | 9/2011 | Song et al. |
| 2011/0270038 A1 | 11/2011 | Jiang et al. |
| 2011/0270179 A1 | 11/2011 | Ouyang et al. |
| 2011/0273556 A1 | 11/2011 | Lyons et al. |
| 2011/0276113 A1* | 11/2011 | Cybulski ............. A61B 18/042 607/101 |
| 2012/0095458 A1 | 4/2012 | Cybulski |
| 2012/0099735 A1 | 4/2012 | Chen |
| 2012/0100729 A1 | 4/2012 | Ouyang et al. |
| 2012/0109007 A1 | 5/2012 | Rhad et al. |
| 2012/0116160 A1 | 5/2012 | Nieman et al. |
| 2012/0130160 A1 | 5/2012 | Borrye |
| 2012/0209065 A1 | 8/2012 | Hosaka et al. |
| 2012/0209066 A1 | 8/2012 | Hosaka et al. |
| 2012/0209067 A1 | 8/2012 | Hosaka et al. |
| 2012/0265009 A1 | 10/2012 | Ouyang et al. |

(56) References Cited

U.S. PATENT DOCUMENTS

| | | |
|---|---|---|
| 2012/0277528 A1 | 11/2012 | Qiao |
| 2012/0289778 A1 | 11/2012 | Chan |
| 2012/0307039 A1* | 12/2012 | Holmes ............... H04N 5/2251 348/82 |
| 2012/0310045 A1 | 12/2012 | Hu et al. |
| 2012/0323073 A1 | 12/2012 | Azuma et al. |
| 2013/0041220 A1 | 2/2013 | Kutsuma |
| 2013/0046316 A1 | 2/2013 | Sullivan et al. |
| 2013/0050455 A1 | 2/2013 | Yagi |
| 2013/0066151 A1 | 3/2013 | Chen |
| 2013/0066152 A1 | 3/2013 | Chen |
| 2013/0072754 A1 | 3/2013 | Okamoto et al. |
| 2013/0079594 A1 | 3/2013 | Motoki |
| 2013/0096376 A1 | 4/2013 | Takei et al. |
| 2013/0225924 A1 | 8/2013 | Simms et al. |
| 2013/0231533 A1 | 9/2013 | Papademetriou et al. |
| 2013/0244453 A1 | 9/2013 | Sakamoto |
| 2013/0253368 A1 | 9/2013 | Are et al. |
| 2013/0289347 A1 | 10/2013 | Ito et al. |
| 2013/0296648 A1 | 11/2013 | Ouyang et al. |
| 2013/0303846 A1 | 11/2013 | Cybulski |
| 2013/0345503 A1 | 12/2013 | Friedrich |
| 2013/0345518 A1 | 12/2013 | Law et al. |
| 2014/0031621 A1 | 1/2014 | Liu |
| 2014/0039253 A1 | 2/2014 | Fang et al. |
| 2014/0073853 A1 | 3/2014 | Swisher et al. |
| 2014/0276207 A1 | 9/2014 | Ouyang et al. |
| 2014/0288460 A1 | 9/2014 | Ouyang et al. |
| 2016/0174819 A1 | 6/2016 | Ouyang et al. |

FOREIGN PATENT DOCUMENTS

| | | |
|---|---|---|
| CN | 2754555 | 2/2006 |
| CN | 201658404 | 12/2010 |
| CN | 201701193 | 1/2011 |
| JP | 10155736 A * | 6/1998 |
| JP | 10-508240 | 8/1998 |
| JP | 2003-88499 | 3/2003 |
| JP | 2007-252559 | 10/2007 |
| JP | 2010-506669 | 3/2010 |
| WO | WO 1994/008512 | 4/1994 |
| WO | WO 2001/029817 | 4/2001 |
| WO | WO 2001/219817 | 10/2001 |
| WO | WO 2008/048688 | 4/2008 |
| WO | WO 2009/150231 | 12/2009 |
| WO | WO 2010/011781 | 1/2010 |
| WO | WO 2011/006052 | 1/2011 |
| WO | WO 2011/038310 | 3/2011 |
| WO | WO 2012/060932 | 5/2012 |
| WO | WO 2012/151073 | 11/2012 |

OTHER PUBLICATIONS

U.S. Appl. No. 12/911,297 entitled "Integrated Hysteroscopy and Endometrial Sampling Device" filed Oct. 25, 2010.
Fourth Office Action from the Chinese Patent Office, Chinese Application Serial No. 201280033333.3 dated Dec. 2, 2016.
EndoSee Corporation Brochure, www.endosee.com, Apr. 2013, 2 pages.
Ethicon Versascope Brochure VS001R2, S/06, 6 pages.
International Search Report and Written Opinion for PCT/US2012/034698, dated Aug. 21, 2012, 14 pages.

* cited by examiner

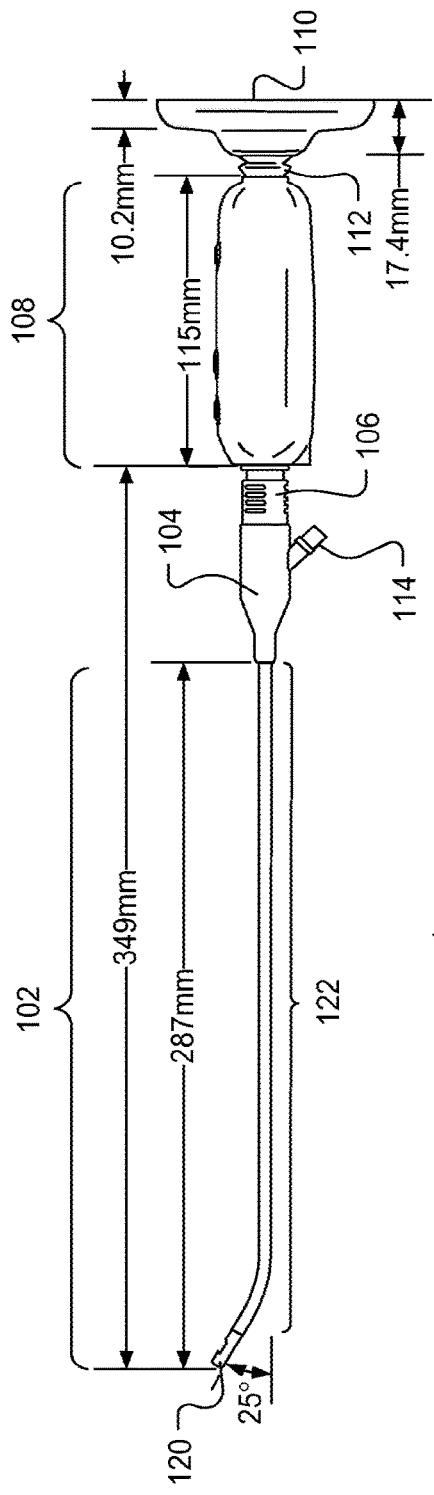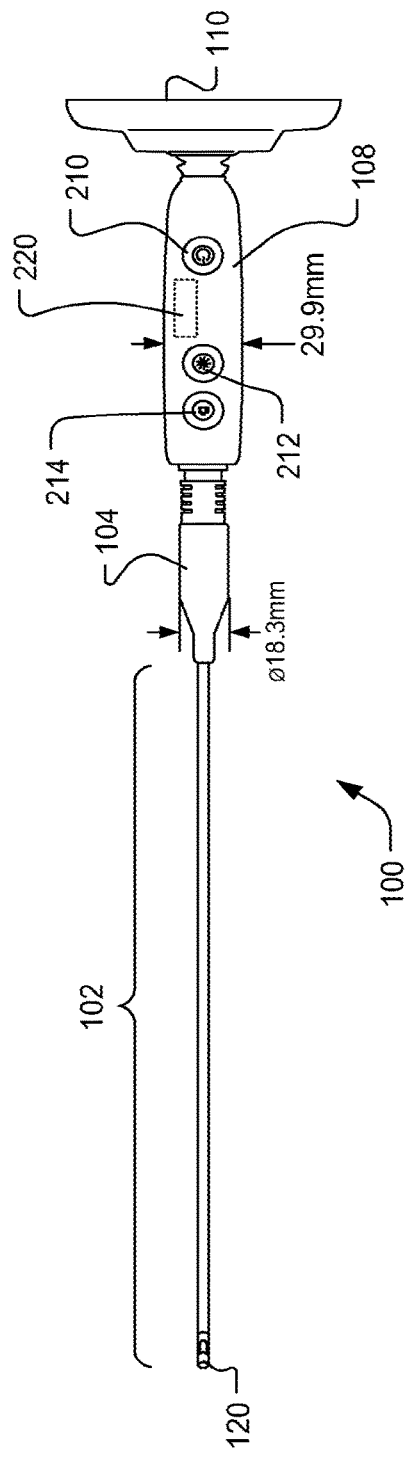

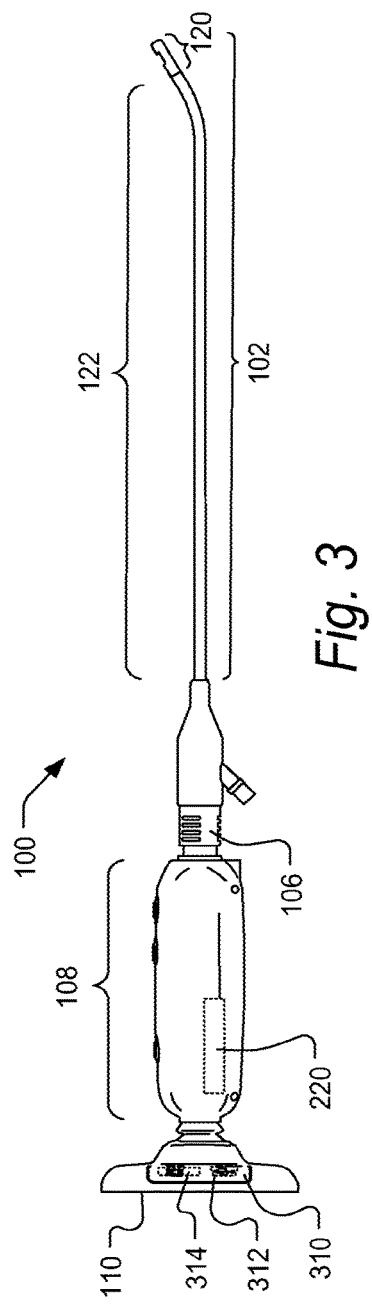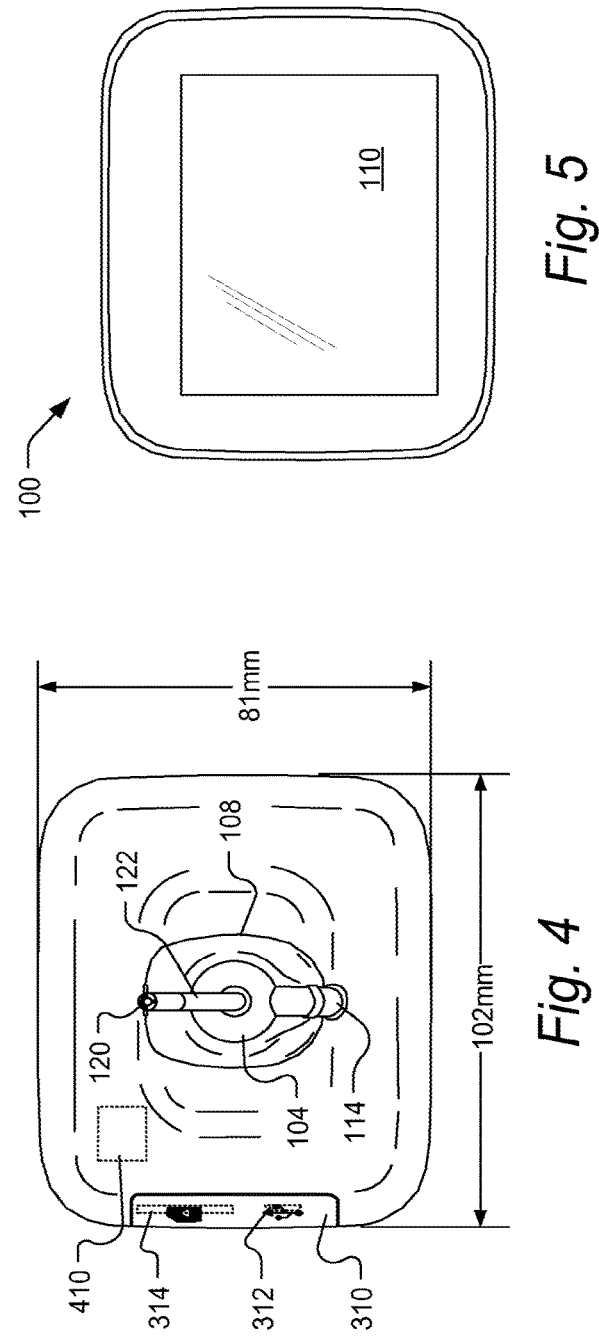
Fig. 3
Fig. 4
Fig. 5

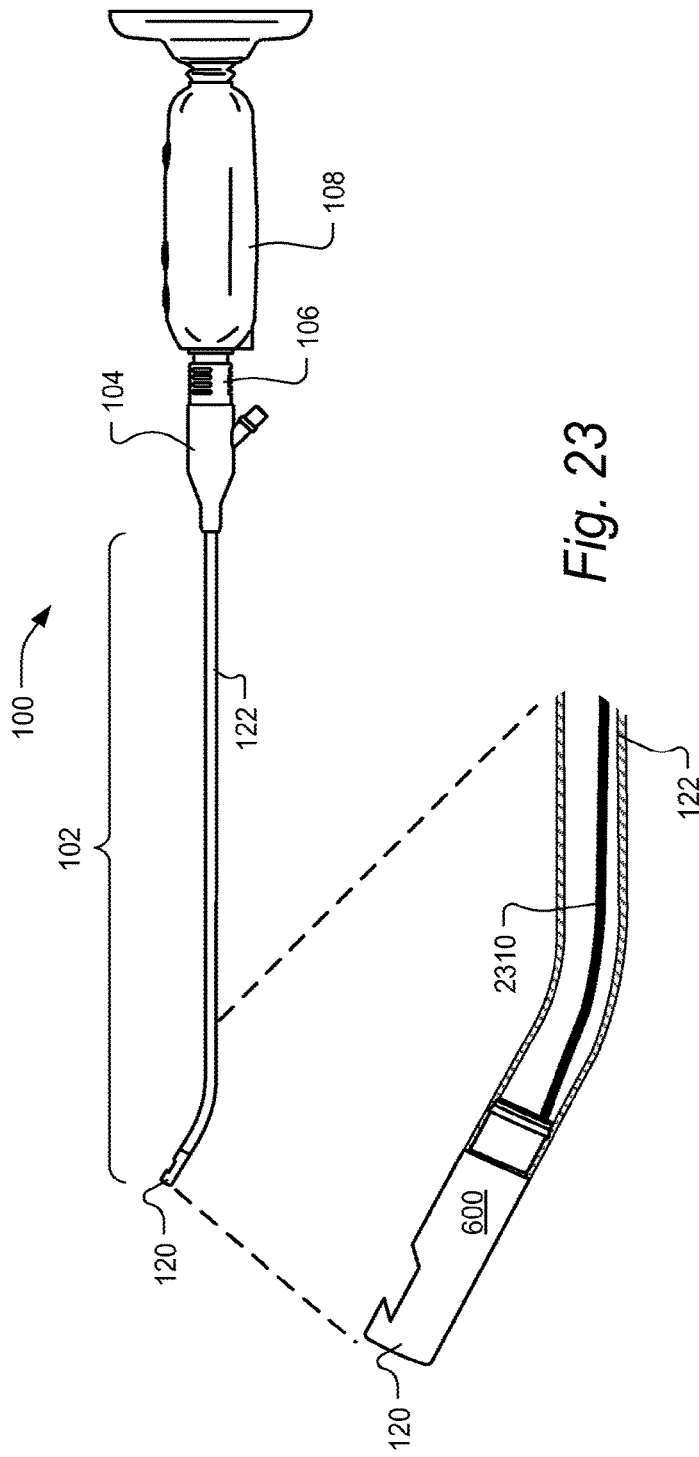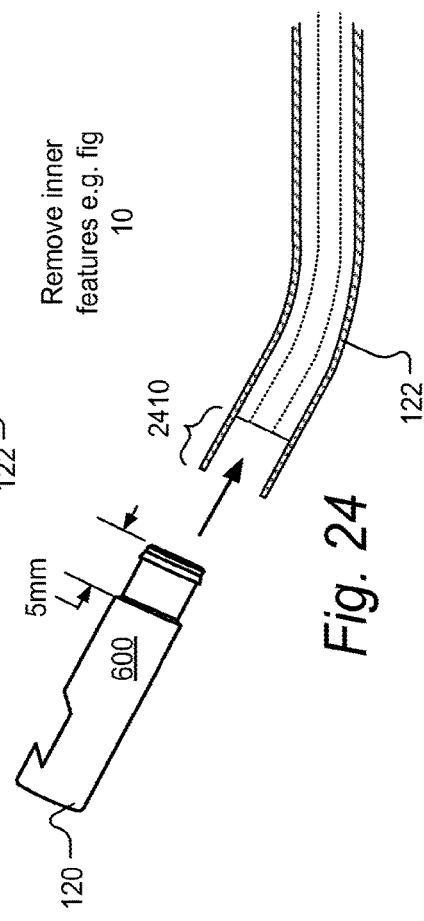

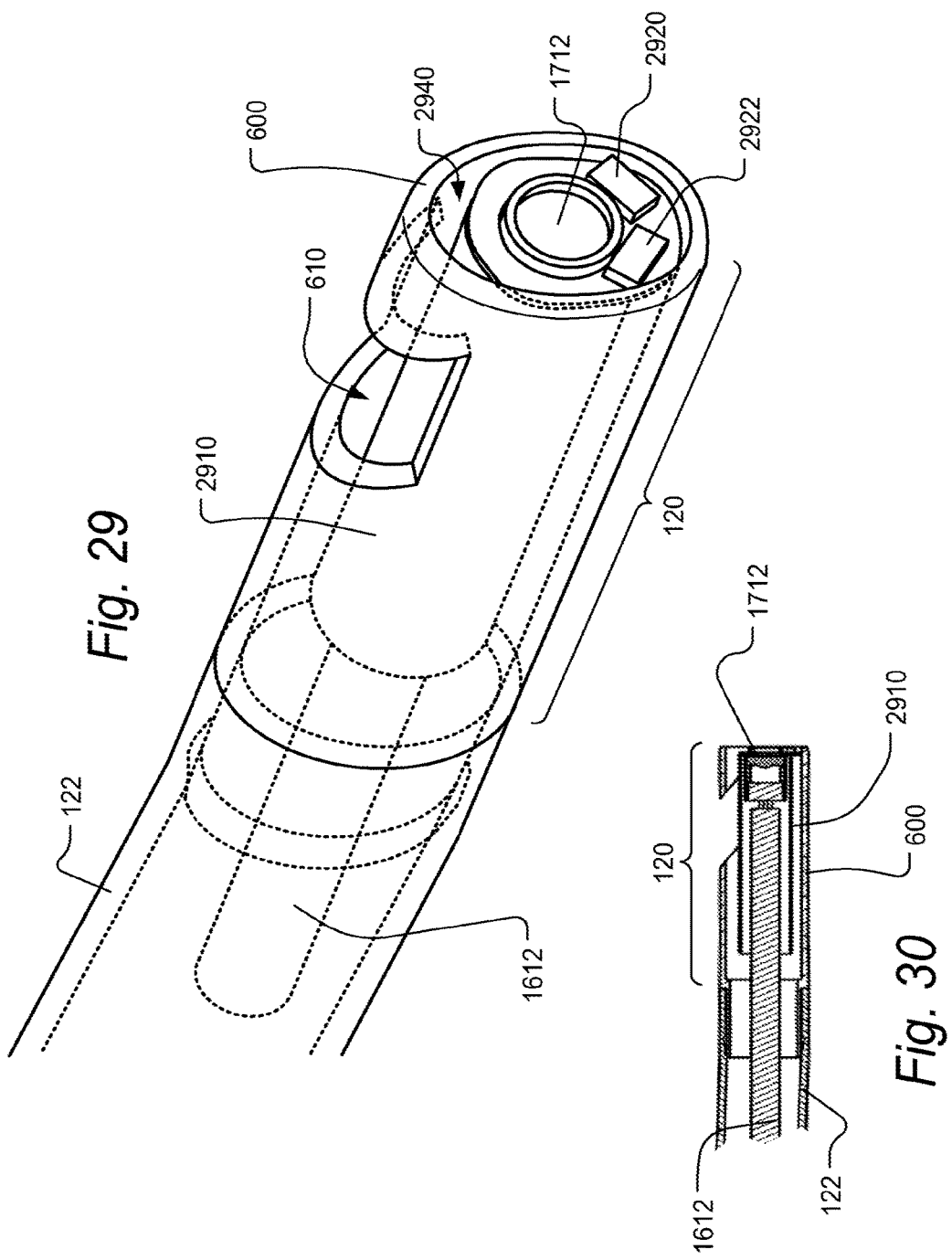

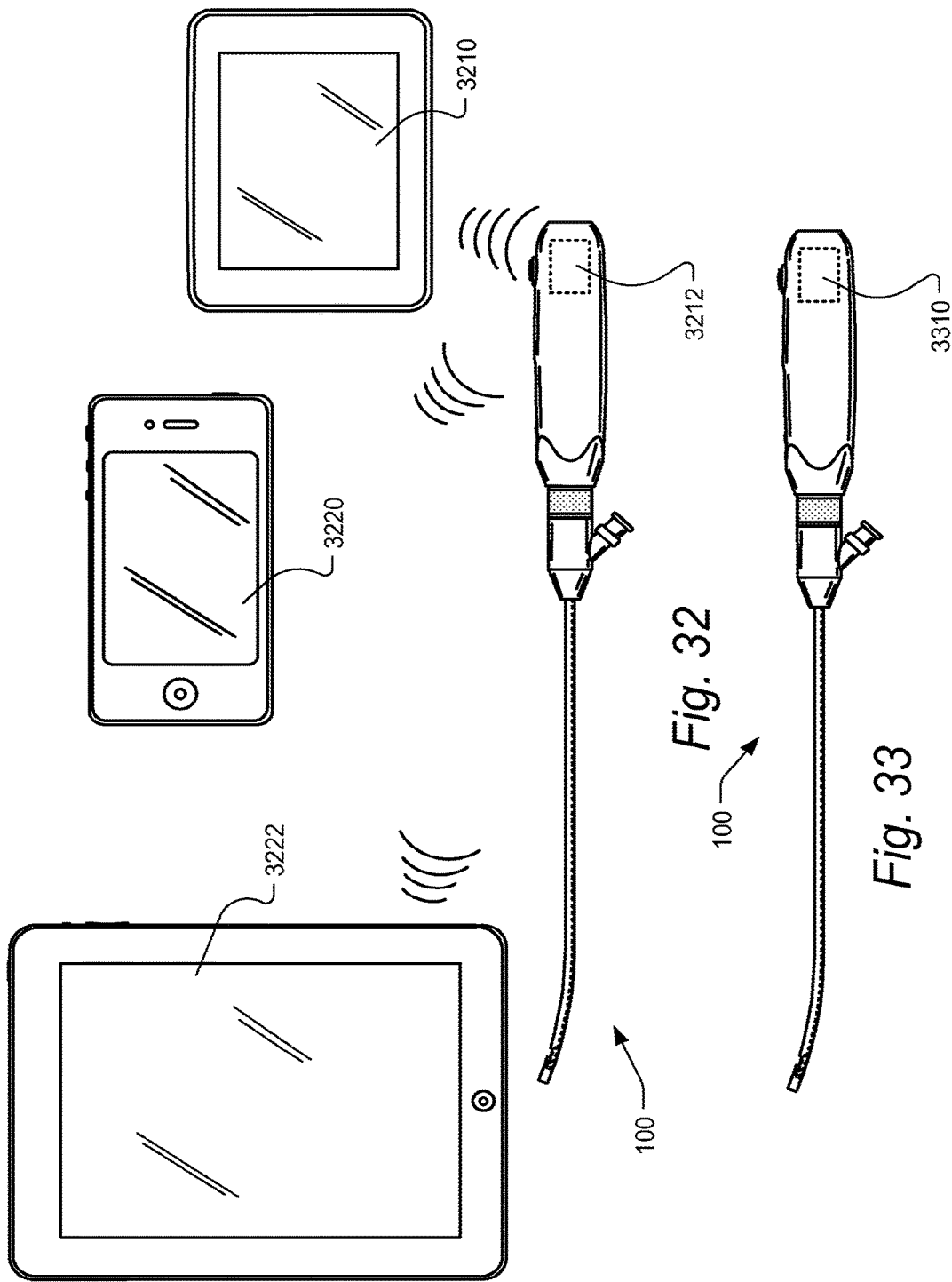

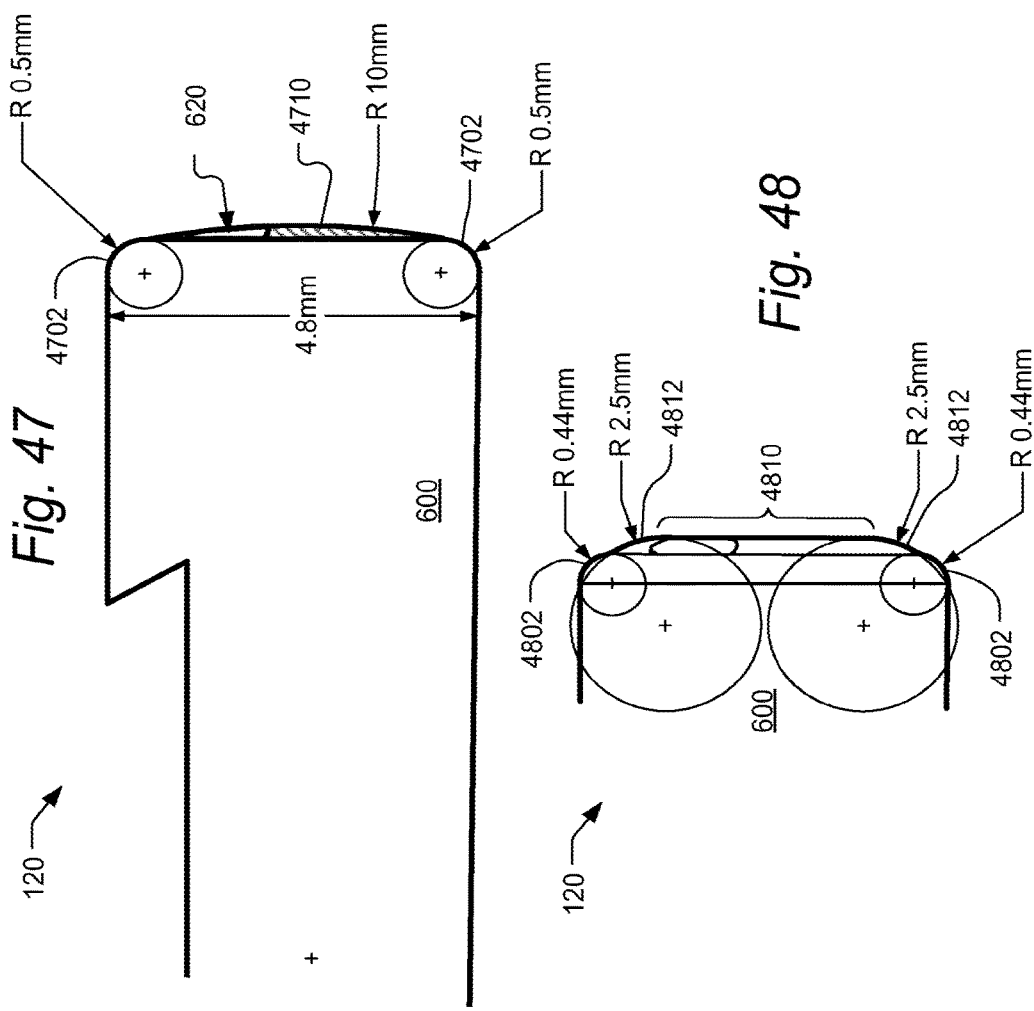

METHOD AND APPARATUS FOR HYSTEROSCOPY AND ENDOMETRIAL BIOPSY

CROSS-REFERENCE TO RELATED APPLICATIONS

This patent application is a continuation of and claims priority under 35 U.S.C. § 120 to U.S. application Ser. No. 14/115,318, filed on Apr. 25, 2014, which is a 371 of International Application No. PCT/US2012/034698, which claims the benefit of and incorporates by reference each of the following applications:

International Patent Appl. No. PCT/US11/51982 filed Sep. 16, 2011;
U.S. Ser. No. 12/911,297, filed Oct. 25, 2010;
U.S. Prov. Ser. No. 61/539,736 filed Sep. 27, 2011;
U.S. Prov. Ser. No. 61/544,280 filed Oct. 7, 2011;
U.S. Prov. Ser. No. 61/550,391 filed Oct. 22, 2011;
U.S. Prov. Ser. No. 61/555,470 filed Nov. 3, 2011;
U.S. Prov. Ser. No. 61/556,167 filed Nov. 4, 2011;
U.S. Prov. Ser. No. 61/570,816 filed Dec. 14, 2011;
U.S. Prov. Ser. No. 61/599,981 filed Feb. 17, 2012;
U.S. Prov. Ser. No. 61/600,593 filed Feb. 18, 2012;
U.S. Prov. Ser. No. 61/611,182 filed Mar. 15, 2012; and
U.S. Prov. Ser. No. 61/623,376 filed Apr. 12, 2012.

The subject matter of this patent specification relates to the subject matter of the following applications, each of which is incorporated by reference herein:

U.S. Prov. Ser. No. 61/418,248, filed Nov. 30, 2010;
U.S. Prov. Ser. No. 61/431,316 filed Jan. 10, 2011;
U.S. Prov. Ser. No. 61/437,687, filed Jan. 30, 2011;
U.S. Prov. Ser. No. 61/444,098, filed Feb. 17, 2011;
U.S. Prov. Ser. No. 61/450,115, filed Mar. 7, 2011;
U.S. Prov. Ser. No. 61/453,533, filed Mar. 16, 2011;
U.S. Prov. Ser. No. 61/476,754, filed Apr. 18, 2011;
U.S. Prov. Ser. No. 61/482,200 filed May 3, 2011;
U.S. Prov. Ser. No. 61/482,309 filed May 4, 2011;
U.S. Prov. Ser. No. 61/485,601 filed May 12, 2011;
U.S. Prov. Ser. No. 61/490,029 filed May 25, 2011;
U.S. Prov. Ser. No. 61/494,400 filed Jun. 7, 2011;
U.S. Prov. Ser. No. 61/506,074 filed Jul. 9, 2011; and
U.S. Prov. Ser. No. 61/515,092 filed Aug. 4, 2011;

The above-referenced provisional and non-provisional patent applications are collectively referenced herein as "the commonly assigned incorporated applications."

TECHNICAL FIELD

The present invention generally relates mainly to a medical device for use in hysteroscopic examinations of the uterus. More particularly, some embodiments relate to a medical device having integrated visualization and endometrial sampling components.

BACKGROUND

Office-based endometrial biopsy is a standard diagnostic procedure used by gynecologists. While efficacious in detection of cancer, endometrial biopsy frequently will not detect endometrial polyps, submucous myomas, and other endometrial pathology. Hysteroscopy, or direct vision of the inside of the uterus (referred to herein as the "uterine cavity" and/or "endometrial cavity"), has been shown to greatly improve diagnostic accuracy. Few gynecologists do office hysteroscopy, however, because of the complexity and expense of the equipment and supplies required. While it is possible to take tiny biopsies through some hysteroscopes that have operating channels, the surgeon usually needs to remove the hysteroscope and then do an endometrial biopsy with a different instrument. The repeated insertion and removal of multiple instruments into the patient's uterine cavity can be uncomfortable for the patient and/or may prolong the time required to complete the hysteroscopy and endometrial sampling procedures compared to performing both procedures without the repeated insertion and removal of different instruments. And, such use of multiple instruments for the same inspection/biopsy procedure requires the expense and inconvenience of buying, stocking and sterilizing such instruments.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

According to some embodiments, an integrated endoscopic apparatus for examining uterine tissues is described. The apparatus includes: an elongate member having a proximal end, a distal end, and being dimensioned so as to facilitate insertion of the distal end through a patient's cervix and into the uterus; a light delivery system adapted to illuminate the uterine tissues being examined; a side-facing sampling opening in the elongate member located and dimensioned so as to facilitate in collection of endometrial tissues; an electronic imaging module positioned on the distal end of the elongate member; and a distal-facing fluid opening positioned on the distal end of the elongate member so as to improve visual inspection using the electronic imaging module by allowing fluid to flow in a distal direction near the lens thereby reducing debris close to the imaging module. According to some embodiments the elongate member includes separated fluid paths for the side-facing opening and the distal-facing opening and/or internal features to enhance fluid flow from the elongate member through the distal-facing fluid opening. According to some embodiments, the electronic imaging module includes a solid-state CMOS sensor, as well as integrated video processing circuitry substantially co-planar with the sensor, to output standard video signals. According to some embodiments, the apparatus includes a handle and an integrated electronic display monitor.

According to some embodiments, an integrated endoscopic apparatus for examining uterine tissues is described that includes: an elongate member having a proximal end, a distal end, and being dimensioned so as to facilitate insertion of the distal end through a patient's cervix and into the uterus; an LED-based light delivery system positioned near the distal end and adapted so as to emit light from at least two points greater than 1 mm apart thereby illuminating uterine tissues being examined; a side-facing sampling opening in the elongate member located and dimensioned so as to facilitate in collection of endometrial tissues; an electronic imaging module positioned on the distal end of the elongate member; and a fluid opening positioned on the distal end of the elongate member so as to improve visual inspection using the electronic imaging module by allowing fluid to flow in a distal direction near the lens thereby reducing debris close to the imaging module. According to some embodiments, the electronic imaging module includes a centrally positioned aperture through which light enters the imaging module, and the light delivery system includes two LEDs positioned on the distal end at opposite sides of the aperture from one another. According to some embodiments, the light delivery system includes a ring-shaped LED module positioned so as to surround the aperture.

According to some embodiments, an integrated endoscopic apparatus for examining uterine tissues is described that includes: an elongate member having a proximal end, a distal end, and being dimensioned so as to facilitate insertion of the distal end through a patient's cervix and into the uterus, wherein the distal end of the elongate member comprises an at least partially hollow shaft member, and a distal tip member wherein the shaft and tip members are separately formed so as to be mated to one another during assembly; a light delivery system adapted to illuminate the uterine tissues being examined; a side-facing sampling opening in the elongate member located and dimensioned so as to facilitate in collection of endometrial tissues; and an electronic imaging module positioned on the distal end of the elongate member. According to some embodiments, a distal-facing fluid opening is positioned on the distal end of the elongate member so as to improve visual inspection using the electronic imaging module by allowing fluid to flow in a distal direction near the lens thereby reducing debris close to the imaging module. According to some embodiments, the shaft and tip members are separately formed for improved assembly yield. The distal tip uses acrylic and the elongate member uses nylon.

According to some embodiments, a method of manufacturing an integrated endoscopic apparatus for examining uterine tissues is described which includes: forming a distal end tip body that is dimensioned to house a light delivery system adapted to illuminate the uterine tissues being examined, and an electronic imaging module positioned on the distal end of the elongate member, the distal end tip body also being formed so as to provide a side-facing sampling opening in the tip body located and dimensioned so as to facilitate in collection of endometrial tissues; forming an elongate shaft member; and securely attaching the distal tip body to the elongate shaft member thereby forming an elongate member of an integrated endoscope dimensioned so as to facilitate insertion of the distal end through a patient's cervix and into the uterus.

According to some embodiments a user-friendly integrated endoscopic apparatus for examining uterine tissues is described that includes an elongate member having a proximal end, a distal end, and being dimensioned so as to facilitate insertion of the distal end through a patient's cervix and into the uterus; a light delivery system adapted to illuminate the uterine tissues being examined; a side-facing sampling opening in the elongate member located and dimensioned so as to facilitate in collection of endometrial tissues; an electronic imaging module positioned on the distal end of the elongate member; a handle having a low overall off-axis profile so as to facilitate easy rotation and tilting in use, the handle including a plurality of buttons to control a plurality of features of the apparatus; and an integrated touch-sensitive electronic display monitor being in electrical communication with the electronic imaging module. According to some embodiments a brightness control button is included with which a user can make a selection from at least three different illumination levels from the light delivery system. According to some embodiments, the plurality of buttons includes a capture button with which a user can select either capturing a still image, or capturing video images, which are stored in a storage device within the apparatus. According to some embodiments a lighted battery status indicator is provided that indicates battery status information to a user using two or more colors. According to some embodiments, a plurality of display screens can be displayed on the integrated touch-sensitive display monitor including a basic menu screen from which a plurality of other screens can be accessed, and one of the plurality of buttons on the handle can be used by a user to jump directly to the basic menu screen.

According to some embodiments, a method for interacting with a user is described including displaying to a user a plurality of screens on a touch-sensitive electronic display monitor, the monitoring being integrated with an endoscopic apparatus. According to some embodiments, user input on the touch sensitive display is received indicating a selection by he user of a stored captured image file (e.g. a still or video image) that the user would like to view. In response to the received user selection, content from the selected stored image file is displayed on the touch sensitive display.

According to some embodiments, an integrated endoscopic apparatus for examining uterine tissues is described including: an elongate member having a proximal end, a distal end, the distal end including a distal face having a rounded edges so as to facilitate safe insertion of the distal end through a patient's cervix and into the uterus, wherein the edges are rounded to a radius of at least 0.25 millimeters; a light delivery system adapted to illuminate the uterine tissues being examined; an electronic imaging module positioned on the distal end of the elongate member; a handle; and an integrated electronic display monitor, the display monitor being in electrical communication with the electronic imaging module. According to some embodiments the edges of the distal face are rounded to a radius of at least 0.35 millimeters, or at least 0.5 millimeters. According to some embodiments the distal face is convex, so as to decrease collection of inadvertent tissue collection on the distal face which could impair visual examination using the imaging module.

DESCRIPTION OF DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIG. 1 is a left side view of a device for combined hysteroscopy and endometrial biopsy according to some embodiments;

FIG. 2 is a top plan view of a device for combined hysteroscopy and endometrial biopsy according to some embodiments;

FIG. 3 is a right side view of a device for combined hysteroscopy and endometrial biopsy according to some embodiments;

FIG. 4 is a distal end view of a device for combined hysteroscopy and endometrial biopsy according to some embodiments;

FIG. 5 is a proximal end view of a device for combined hysteroscopy and endometrial biopsy according to some embodiments;

FIGS. 23 and 24 show details of the a device for combined hysteroscopy and endometrial biopsy having separate tip and shaft assemblies, according to some embodiments;

FIGS. 29 and 30 show further details of a distal tip for a device for combined hysteroscopy and endometrial biopsy, according to some embodiments;

FIGS. 31-33 show a single-use device for combined hysteroscopy and endometrial biopsy, according to various embodiments;

FIGS. 36 and 37 are a perspective view and a side view, respectively, of the handle and display docked to a base station, according to some embodiments;

FIGS. 47-48 are side views showing details of the shapes of distal tips of a hysteroscopy device, according to some embodiments.

DETAILED DESCRIPTION

Figure 6:
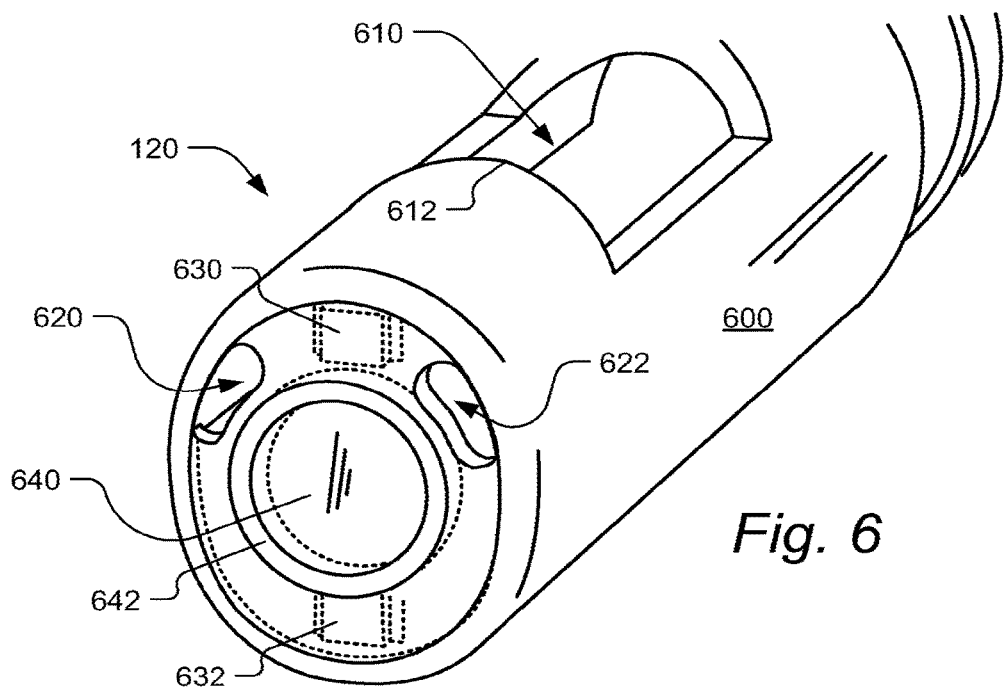
FIG. 6 is a prospective view of a distal tip of a device for combined hysteroscopy and endometrial biopsy according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding work, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

FIG. 1 is a left side view of a device for combined hysteroscopy and endometrial biopsy according to some embodiments. Many of the elements of the embodiments of hysteroscope 100 shown in FIG. 1 are the same as or similar to those discussed in the embodiments described in the commonly assigned incorporated applications, and such elements may not be described or may only briefly be described. It will also be appreciated that the aspects of the embodiments described in the commonly assigned incorporated applications may also apply to the embodiments described herein.

The device 100 is particularly advantageous for enabling a physician to perform an efficient combined hysteroscopic examination and an endometrial biopsy, although it is to be appreciated that other uses for hysteroscope 100 are within the scope of the present teachings. The hysteroscope 100 can bring about substantial efficiencies in terms of keeping equipment costs low and keeping the time required to perform the procedure modest, while at the same time providing the opportunity for better endometrial sample quality over conventional "blind" endometrial sample collection methods. Hysteroscope 100 includes a cannula 102, fluid hub 104, sliding connector 106, handle body 108, display mount 112 and display 110. The cannula 102 is made of a distal tip 120 and a shaft 122. The fluid hub includes one or more fluid ports 114 for delivering fluid into the device and thus into the uterus and/or for applying suction to extract fluid and tissue samples from the uterus. As shown the shaft 122 is curved near its distal end, for example having a 25 degree bend as shown. According to some embodiments, a bend of between 15 and 35 degrees near the distal end has been found to be suitable for many applications. The distal tip 120 includes a video camera assembly, lighting elements and fluid ports for in-flow (i.e. out of the device 100 and into the patient) and out-flow (i.e. into the device 100 and out of the patient). A sampling port on the upper side of the distal tip 120 also includes a cutting portion, which aids in tissue sample collection, as described in more detail below. The tip 120 includes a housing body that is made from acrylic, according to some embodiments. The shaft 122 is made from nylon, according to some embodiments. According to some embodiments the display 110 is a touch screen display, and is able to tilt upwards and downwards by, for example, about 45 degrees. According to some embodiments, in FIG. 1 as in other figures herein, various dimensions are shown that have been found to be suitable for many applications, but those skilled in the art may vary those dimensions without departing from the teachings of this patent specification. According to some embodiments, the cannula 102 (including the camera assembly, LED lighting and fluid ports integrated into the distal tip 120), fluid hub 104 and sliding connector 106 are designed for a single-use. According to these embodiments the cannula 102, fluid hub 104 and connector 106 are delivered to the medical practitioner in pre-sterilized package and are intended to be disposed of after a single-use, while the handle 108 and display 110 are designed to be re-used many times.

Figure 36:
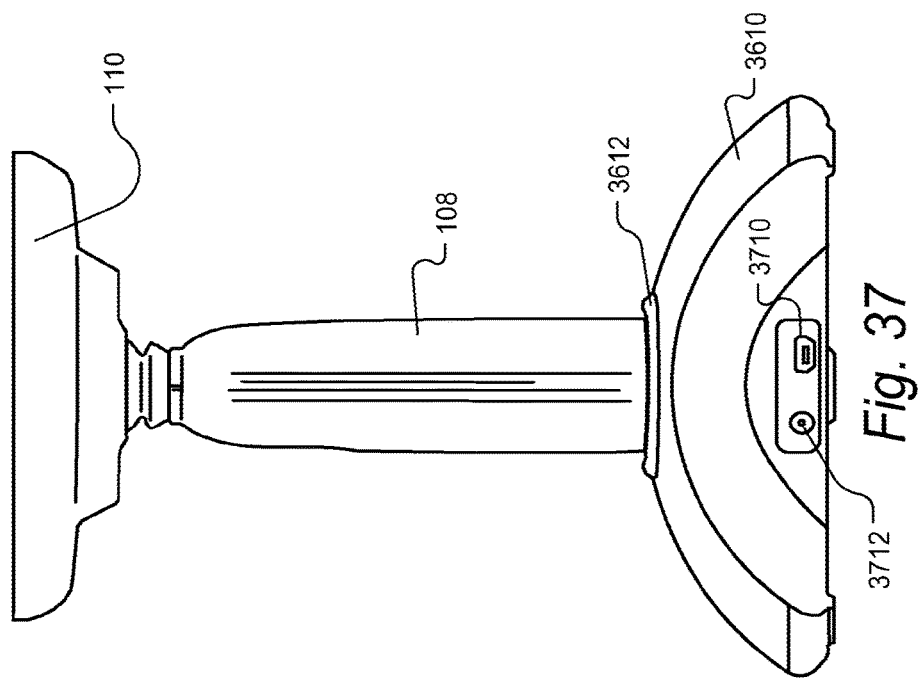
Figure 37:
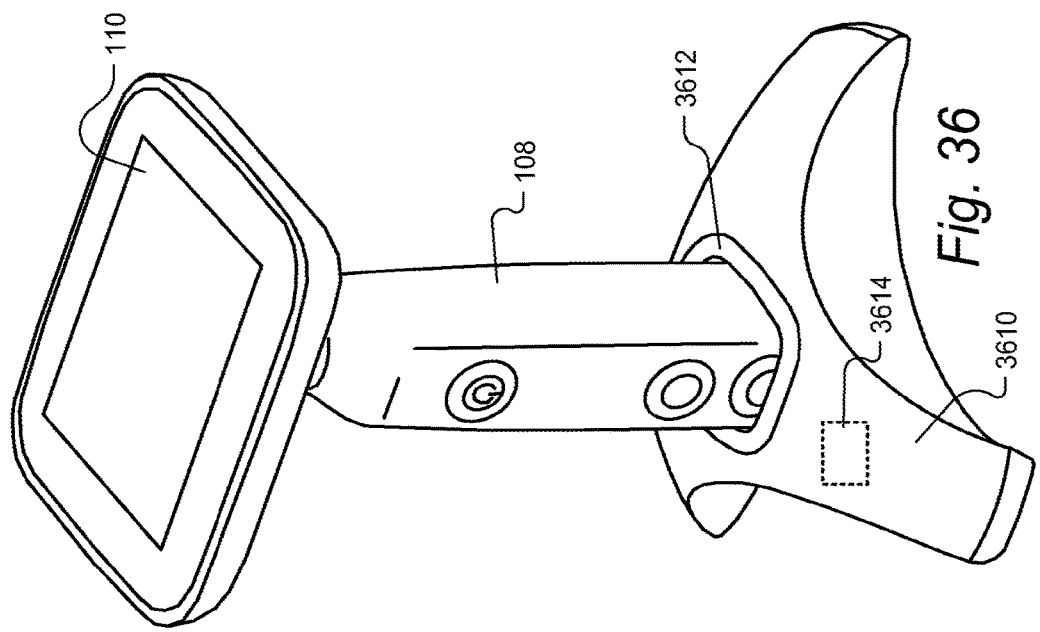
Figure 41:
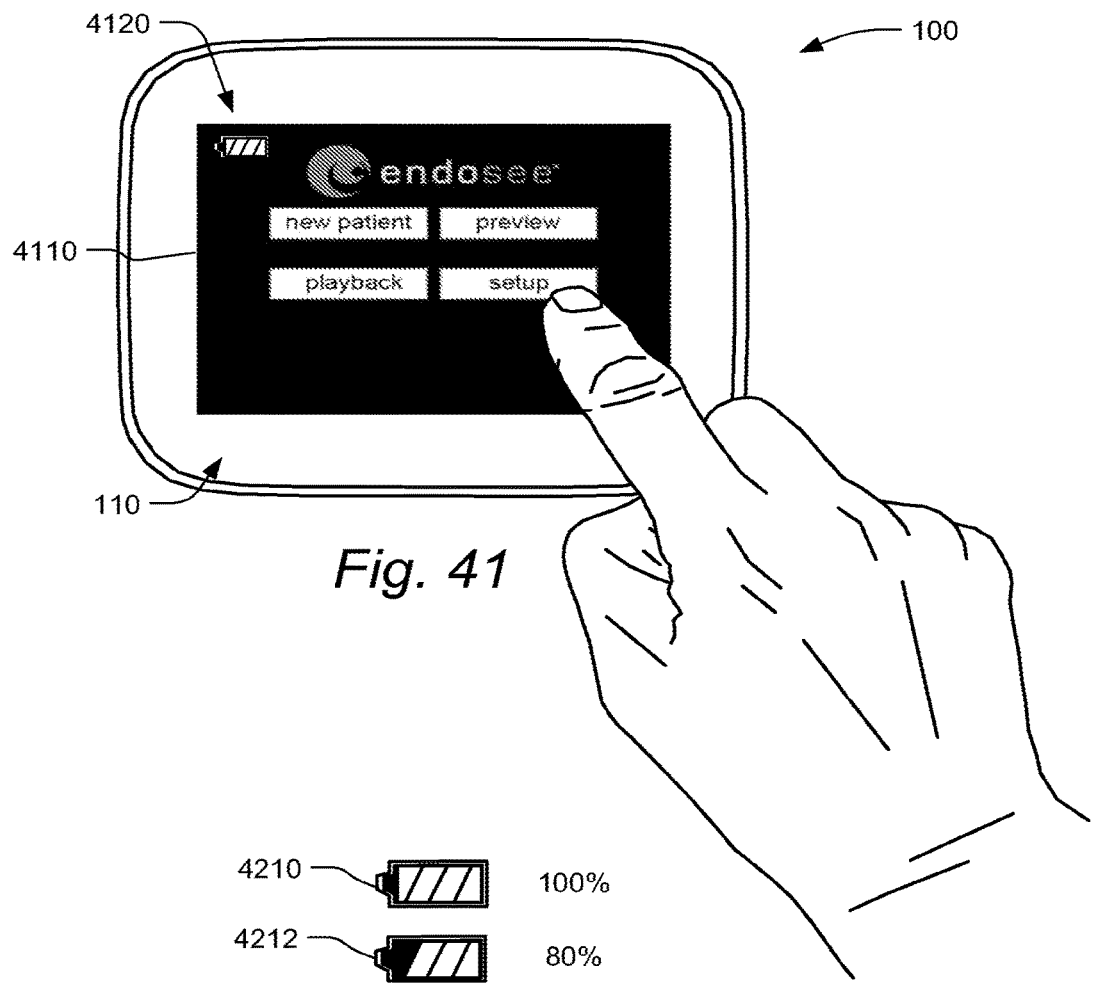
FIG. 41 is shows a display screen user interface for a hysteroscopy device, according to some embodiments.

FIG. 2 is a top plan view of a device for combined hysteroscopy and endometrial biopsy according to some embodiments. In this view, three control buttons are shown on the handle body 108. In particular, ON/OFF button 210 is used to toggle the device 100 on or off. According to some embodiments, the power ON/OFF button 210 is backlit using two differently colored LEDs to indicate the status of rechargeable battery 220 to the user. For example, green backlighting can be used to indicate the battery level is OK and red backlighting can be used to indicate the battery 220 is low (for example, less than 30% capacity remaining, such as used for icon 4218 shown in FIG. 42 infra). According to some embodiments the capacity of battery 220 is about 2500 mAh. According to some embodiments, the LED lighting of button 210 can also be used to indicate battery charging status during re-charging of the battery 220 from an external power source, such as when docked to a base station such as shown in FIGS. 36-37, infra, or when connected to a USB powered source using port 312 shown in FIGS. 3-4 infra. In this case, the backlighting LED shows red while charging the battery and green when the battery 220 is fully charged. According to some embodiments, the ON/OFF button 210 doubles as a "home" button, such that a shorter press, such as 1 second or less, of button 210 brings up a home screen menu on the display 110, as shown in FIG. 41, infra, while a longer press will turn the unit off.

LED brightness control button 212 is used to control the brightness of the LEDs on the distal tip 120. According to some embodiments a total of four different LED illumination levels has been found to be suitable and the single button 212 controls the level by cycling through the levels, changing the illumination level with each button press. The Snap/Video button 214 is used to capture still images and/or video from the camera in tip 120. According to some embodiments, pressing Snap/Video button 214 for three seconds or less captures a single still photo, while pressing button 214 for longer than three seconds starts video recording. When video is being recorded, a single press of button 214 stops video capture. Further details of the user interface which includes the buttons 210, 212 and 214 as well as the interactive touch screen display 110 are described with respect to FIGS. 41-46 infra. According to some embodiments, an audible acknowledgement signal is associated with presses of the buttons 210, 212 and 214. For example, a single "beep" is sounded when any of the buttons (including software buttons such as shown in FIGS. 41 and 43-46 infra.) except for double beeps when either the Snap/Video button 214 or an OK software button is pressed.

FIG. 3 is a right side view of a device for combined hysteroscopy and endometrial biopsy according to some embodiments. On the side of the display 110 is a rubber flap 310 that covers mini-USB port 312 and SD card slot 314. Flap 310 forms a fluid seal around the edge of the opening. Beneath the flap 310, the mini-USB port 312 serves multiple purposes including video-out to an external display, connector to an AC adapter for charging the rechargeable battery 220, and/or as a port to a host PC for downloading and uploading images, video and/or settings, as well as for charging the rechargeable battery 220. The SD card slot 314 is used to accept flash memory cards used to store images, video and/or settings for the device 100. According to some embodiments a standard size high-capacity (SDHC or SDXC) slot is provided, although smaller form factors such as Mini SD or Micro SD cards, or other types of storage media can be used.

FIG. 4 is a distal end view of a device for combined hysteroscopy and endometrial biopsy according to some embodiments. The tip 120 and shaft 122 can be seen, as well as the fluid hub 104, fluid port 114 and handle body 108. The SD card/USB port flap 310 is also shown on the side of the display body. Also shown, according to some embodiments is photo/video processing circuitry 410 that can be used to enhance or otherwise manipulate standard video signals and/or images received from the camera module in tip 120.

FIG. 5 is a proximal end view of a device for combined hysteroscopy and endometrial biopsy according to some embodiments. Touch-sensitive screen 110 is preferably 3.5 inches (diagonally) in size.

FIG. 6 is a prospective view of a distal tip of a device for combined hysteroscopy and endometrial biopsy according to some embodiments. Distal tip 120 includes a tip housing 600 that is made from acrylic, according to some embodiments. On the tip side of the tip 120 is the sampling port 610 used to draw fluid out of the patient's uterus as well as collect tissue. The sampling port 610 includes a cutting edge 612, which is sharp and positioned so as to facilitate collection of the endometrial sample by scraping. On the distal end of the tip 120 is camera assembly 640. Two LEDs 630 and 632 are positioned above and below the camera to evenly illuminate the uterine tissue for visual inspection. A light shield 642 acts a lens hood and shields direct light from the LEDs 630 and 632 from entering the aperture of the camera 640.

One problem in performing visual inspections of endometrial tissues, and particularly in situations where the endometrial medium, consisting of free tissue, loosely attached tissue and/or fluid, is relatively thick, is that light reflected from tissue particles suspended close to the lens can appear overly-bright and therefore impair imaging of other tissue surfaces. According to some embodiments, two forward facing fluid ports, 620 and 622 are provided to allow fluid to exit the tip and tend to push suspended particulate matter away from the camera so as to enhance image and video capture by camera 640. In some cases some tissue debris may collect on the distal surface such that imaging would be impaired in such cases the forward facing ports are useful in clearing away such collected tissue. Also it has been found that the forward facing ports are helpful in aiding insertion of the cannula in many cases as the fluid provides lubrication as well as a partial distending of tissues just ahead of the distal tip during insertion. Since the forward facing ports improve visualization, the risk of accidental damage to the uterus is greatly reduced.

Figure 7:
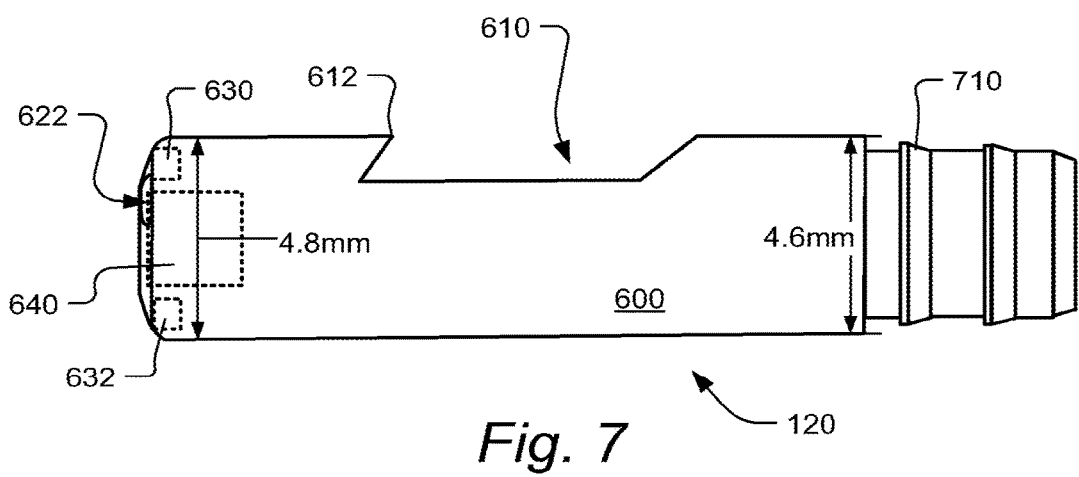
FIG. 7 is a left side view of a distal tip of a device for combined hysteroscopy and endometrial biopsy according to some embodiments.

FIG. 7 is a left side view of a distal tip of a device for combined hysteroscopy and endometrial biopsy according to some embodiments. The acrylic body 600 of the tip 120 preferably includes one or more ridges 710 to aid in securely fastening the tip 120 to the shaft 122 (not shown).

Figure 8:
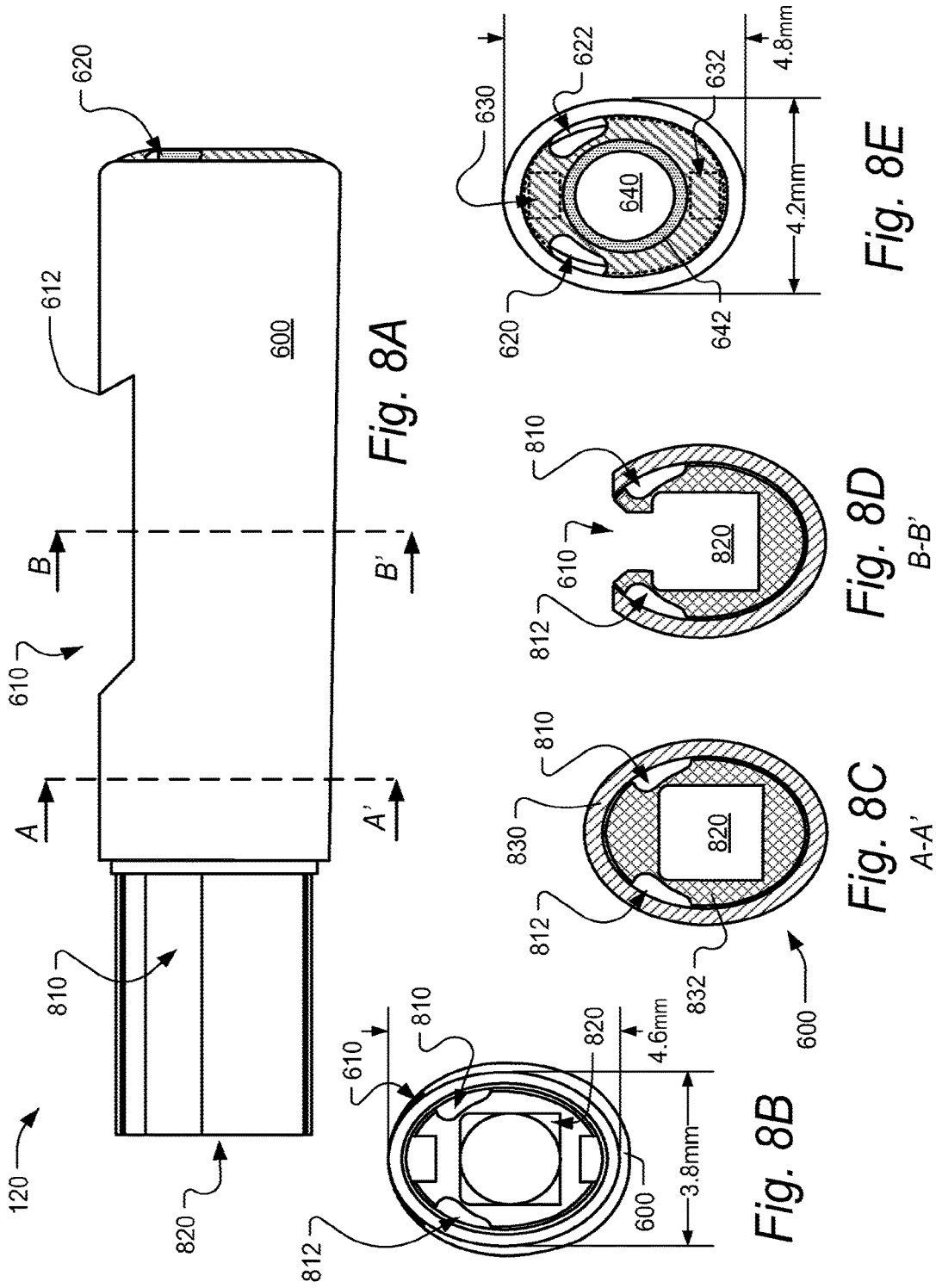
FIG. 8A is a right side view of a distal tip assembly of a device for combined hysteroscopy and endometrial biopsy according to some embodiments.
FIGS. 8B-8E are further views of the distal tip assembly of a device for combined hysteroscopy and endometrial biopsy according to some embodiments.

FIG. 8A is a right side view of a distal tip assembly of a device for combined hysteroscopy and endometrial biopsy according to some embodiments. In these embodiments, the forward facing in-flow (out of the device) fluid ports are connected to a separate fluid channel to enhance control over the fluid flowing into and out of the device 100. The tip 120 in this case includes separated fluid channels for fluid in-flow and out-flow. In particular a separate fluid channel 810, which runs along the upper right side, is connected to the front-facing fluid port 620, and another fluid channel, not shown, is connected to the other front-facing fluid port 622, not shown. A central fluid channel 820 is connected to the side sampling port 610.

FIGS. 8B-8E are further views of the distal tip assembly of a device for combined hysteroscopy and endometrial biopsy according to some embodiments. FIG. 8B is a proximal end view of the tip 120 shown in FIG. 8A. The tip body or housing 600 includes two in-flow (out of the device and into the patient) channels 810 and 812 that are fluidly connected to the two in-flow front-facing ports, and a central channel 820 that is fluidly connected to the sampling port 610. The central channel 820 is also used to run a video and control cable from the camera assembly towards the handle and the display. FIG. 8C is a sectional view of the distal tip along the line A-A' shown in FIG. 8A. Note that the tip housing 600 is made of an outer sleeve 830 and a core 832, according to some embodiments. FIG. 8D is a sectional view of the distal tip along the line B-B' shown in FIG. 8A, and shows the connection between the central fluid channel 820 and the sampling port 610. FIG. 8E is a distal end view of the tip assembly 120 shown in FIG. 8A. According to some embodiments, the tip 120 outer dimensions are slightly larger toward the distal end. For example, the tip body 600 measures 3.8 mm×4.6 mm at the proximal end, shown in FIG. 8B, and measures 4.2 mm×4.8 mm at the distal end, shown in FIG. 8E.

Figure 9:
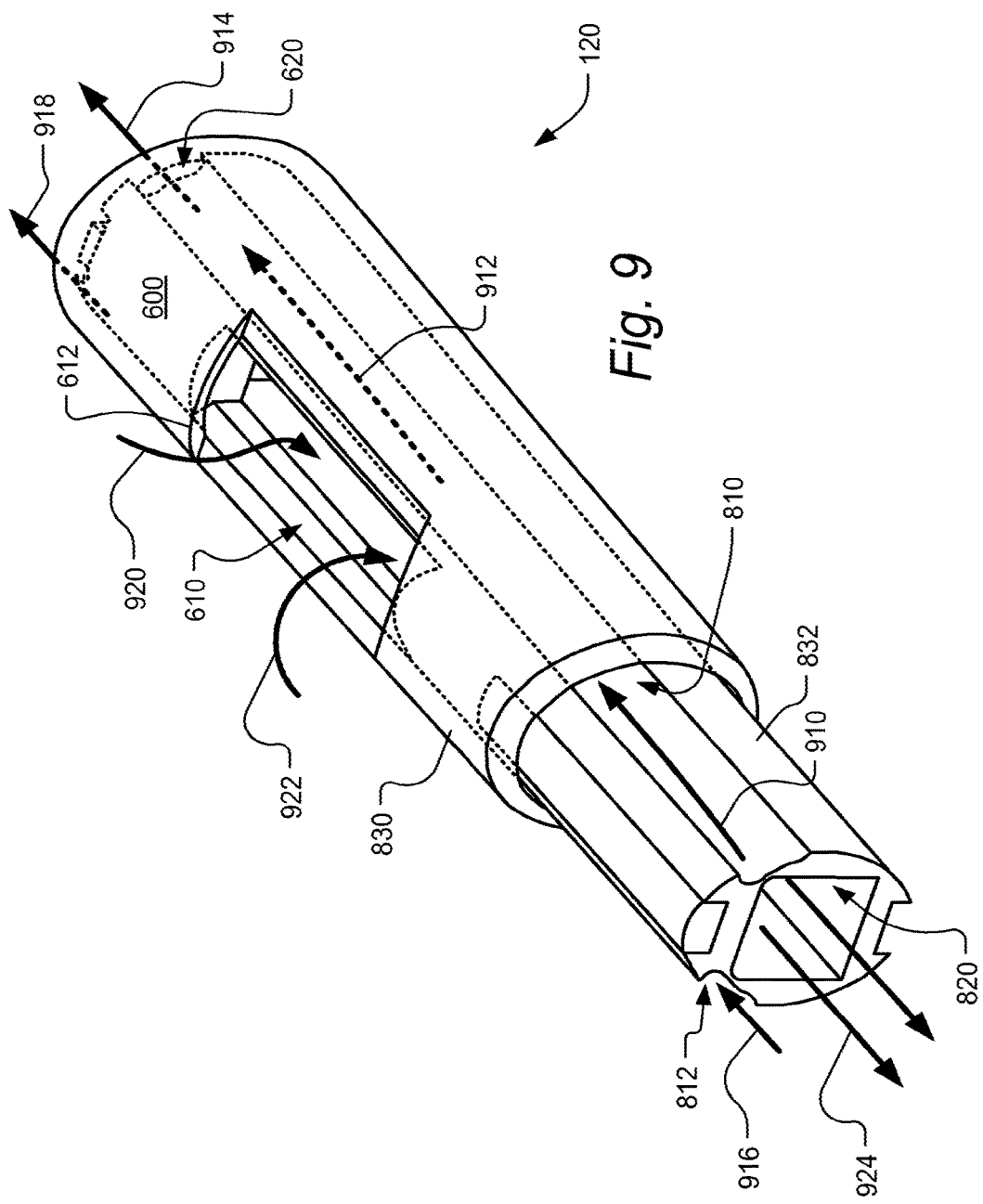
FIG. 9 is perspective view of a distal tip of a device for combined hysteroscopy and endometrial biopsy according to some embodiments.

FIG. 9 is perspective view of a distal tip of a device for combined hysteroscopy and endometrial biopsy according to some embodiments. This view of the distal tip assembly 120 shows fluid direction arrows such as arrows 910, 912 and 914 for fluid flowing through channel 810 and out of front-facing port 620. The arrows 916 and 918, similarly, show the direction of fluid flowing in channel 812. The arrows 920, 922 and 924 show the direction of fluid from sampling port 610 and through the central channel 820.

Figure 10:
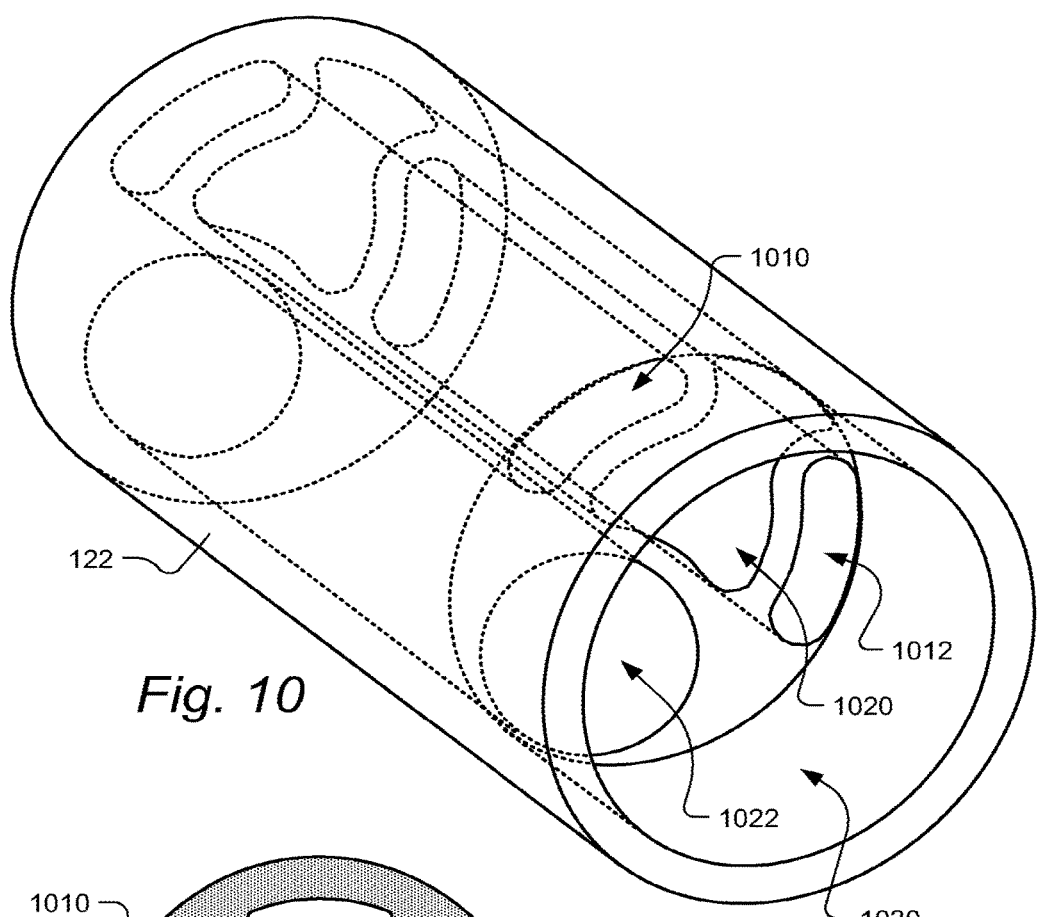
FIGS. 10 and 11 show details of the internal structure of the shaft having separated fluid channels of a device for combined hysteroscopy and endometrial biopsy according to some embodiments.
Figure 11:
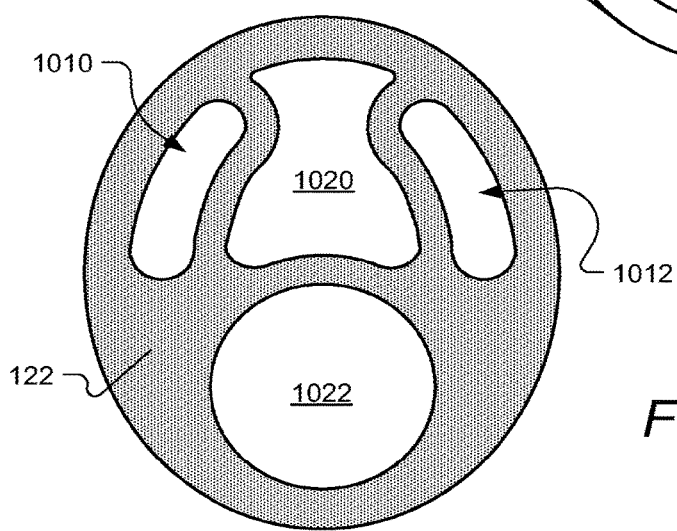

FIGS. 10 and 11 show details of the internal structure of the shaft having separated fluid channels of a device for combined hysteroscopy and endometrial biopsy according to some embodiments. FIG. 10 is a perspective view of the distal end of the shaft 122. The distal end 1030 of the shaft 122 has the internal structure removed so as to be able to mate with the proximate end of the tip 120. The shaft 122 has separate channels 1010 and 1012 that are aligned so as to fluidly mate with channels 810 and 812 respectively on tip 120. The upper central channel 1020 is used for the out-flow fluid (i.e. into the device) for removing fluid from the uterus and/or to provide negative pressure for tissue sample collection. The channel 1020 is thus positioned to fluidly mate with central channel 820. Also included is a separate channel 1022 that is used to house the video and camera control cable, which also passes through the central channel 820 of tip 120. FIG. 11 is a cross section of the shaft 122. According to some embodiments, the shaft 122 is made from extruded nylon.

Figure 12:
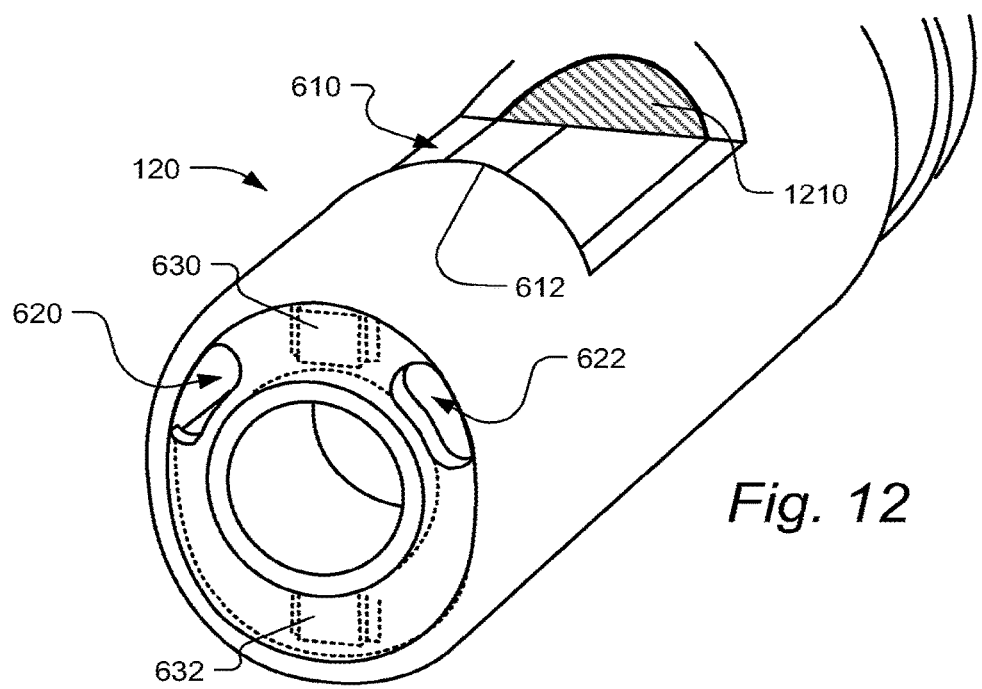
FIGS. 12, 13 and 14 show internal structures of a distal tip of a device for combined hysteroscopy and endometrial biopsy according to some alternate embodiments.
Figure 13:
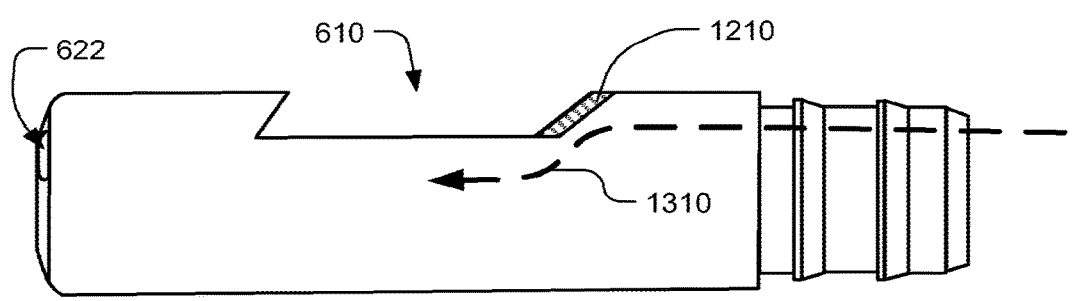
Figure 14:
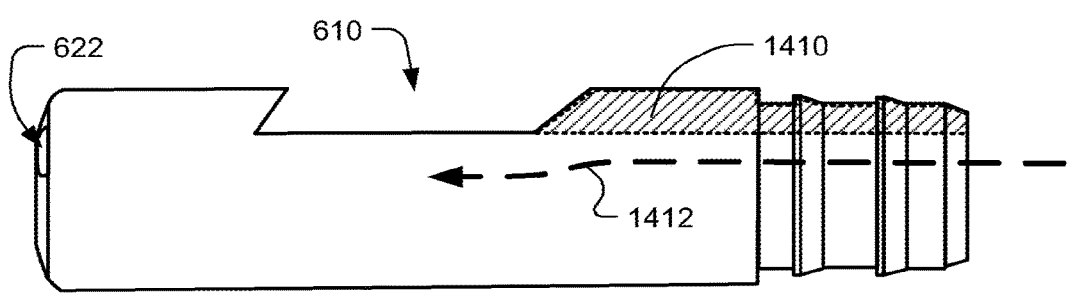

FIGS. 12, 13 and 14 show internal structures of a distal tip of a device for combined hysteroscopy and endometrial biopsy according to some alternate embodiments. FIGS. 12-14 show two embodiments wherein the in-flow and outflow paths are not separated as in the case of the embodiments of FIGS. 8A-E and 9. In the case where the flow paths are not separated, the tip 120, shaft 122 and fluid hub 104 can be more structurally simplified. However, due to the relative sizes of the forward facing fluid ports 610 and 612 on the one hand and the side-facing port 620 on the other, certain structural elements may be included to ensure adequate fluid flow out of the front facing ports 610 and 612 during times when useful to improve visual inspection. In the case of FIGS. 12 and 13, an element 1210 is included just behind the sampling port 610 to direct the fluid towards the forward-facing ports as shown by arrow 1310 in FIG. 13. In the case of FIG. 14, the upper section 1410 is filled in solid so as to aid in directing the fluid towards the forward-facing ports as shown by arrow 1412.

Figure 15:
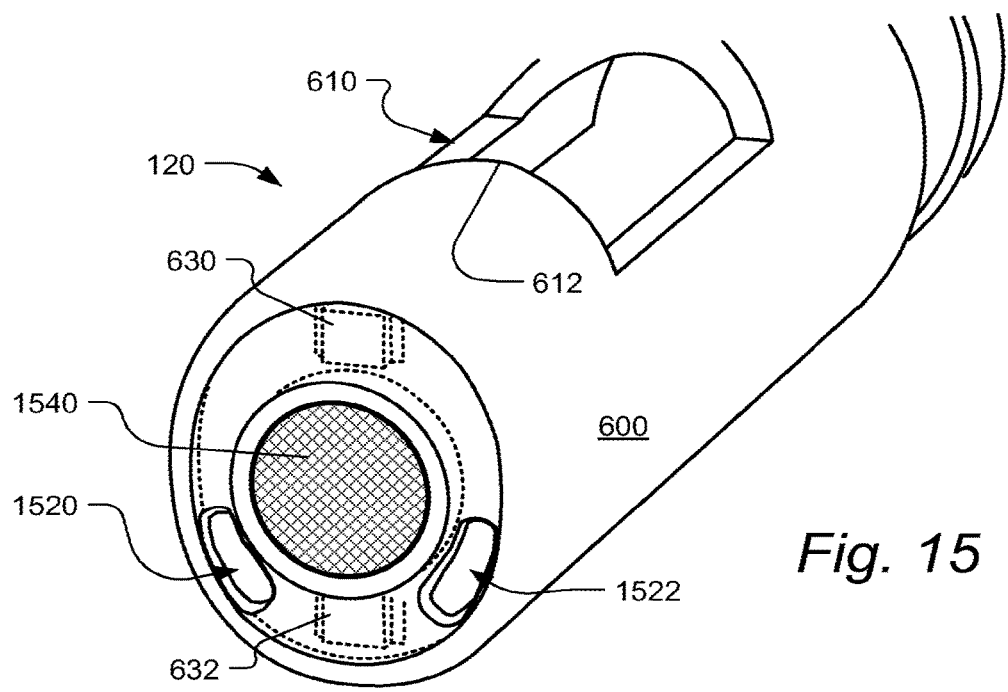
FIGS. 15-16 show a distal tip of a device for combined hysteroscopy and endometrial biopsy according to some alternate embodiments.
Figure 16:
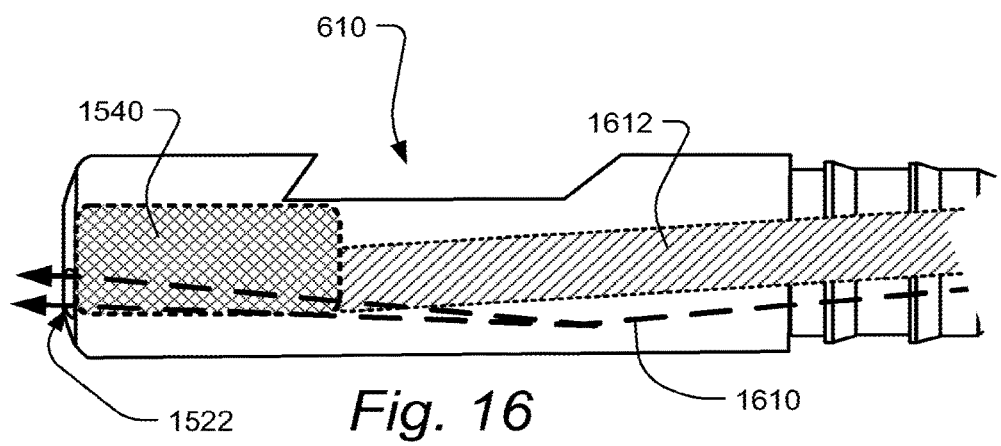

FIGS. 15-16 show a distal tip of a device for combined hysteroscopy and endometrial biopsy according to some alternate embodiments. FIGS. 15-16 show a further embodiment wherein the in-flow and out-flow paths are not separated as in the case of the embodiments of FIGS. 8A-E and 9. In this case, the two forward-facing fluid ports 1520 and 1522 are positioned lower on the distal tip 120 such that the camera module 1540 and the video cable 1612 tend to force the in-flow direction fluid (i.e. out of the tip 120) under the cable 1612 and toward the ports 1520 and 1522 rather than out of the side-facing sampling port 610. The arrows 1610 show example fluid flow paths in the in-flow direction (out of the device). According to other embodiments other internal structures can be provided in addition to or in place of those shown in shown in FIGS. 12-16 to enhance flow through the forward facing ports.

Figure 17A:
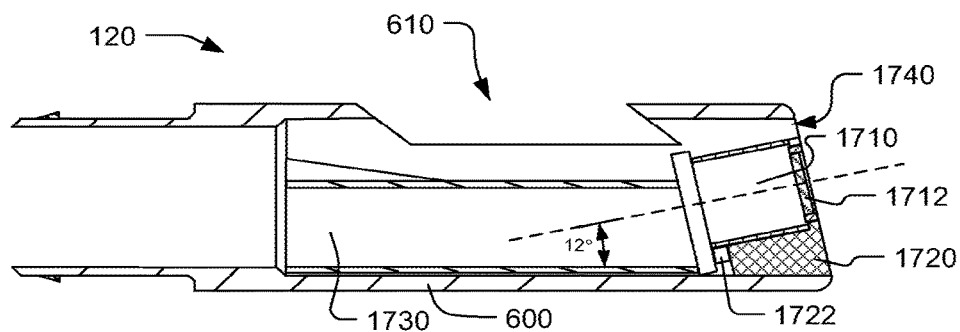
FIGS. 17A-17B show a distal tip of a device for combined hysteroscopy and endometrial biopsy having an up-tilted camera module, according to some embodiments.
Figure 17B:
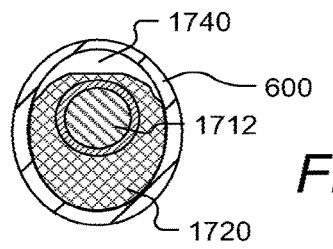

FIGS. 17A-17B show a distal tip of a device for combined hysteroscopy and endometrial biopsy having an up-tilted camera module, according to some embodiments. In FIG. 17A, it can be seen that camera 1710 is tilted up at an angle of, e.g., 12 degrees from the longitudinal axis of the tip body or housing 600. The upwards tilting of the camera increases the effective field of view of the device. Also shown in FIGS. 17A and 17B is a glass cover 1712 of camera module 1710. A light guide 1720 is also used to diffuse light from one or more LEDs, such as LED 1722. The light guide 1720, as shown in FIG. 17B surrounds the camera module 1710. The light guide 1720 can be made of glass or a polymer, for example. Also shown in this example is a forward facing fluid port 1740 which is useful in directing fluid in a forward direction so as to enhance visual inspection.

Figure 18A:
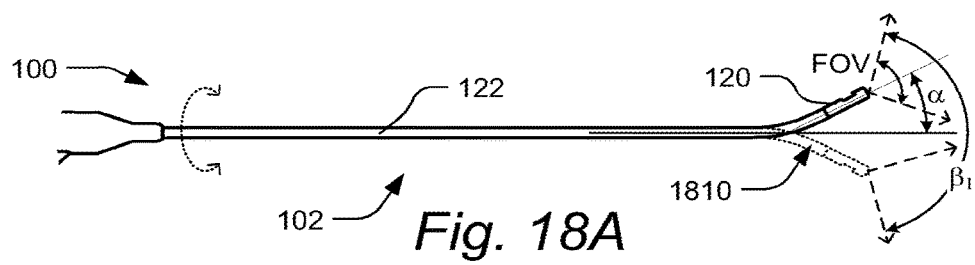
FIGS. 18A-18B illustrate how camera tilting effects effective field of view for a device for combined hysteroscopy and endometrial biopsy, according to some embodiments.
Figure 18B:
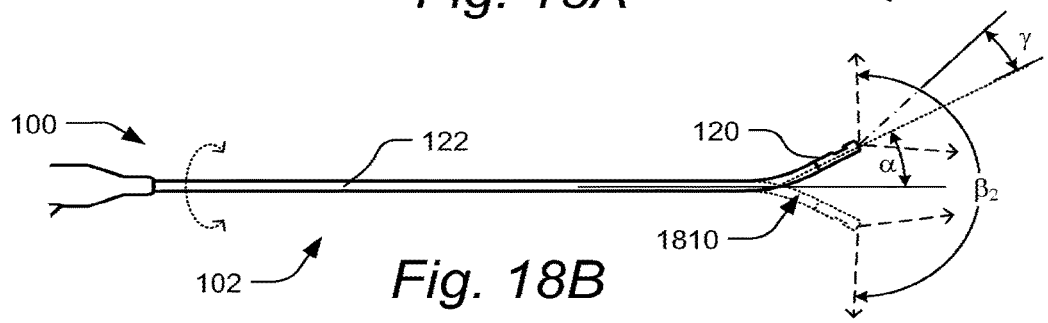

FIGS. 18A-18B illustrate how camera tilting provides a larger effective field of view for a device for combined hysteroscopy and endometrial biopsy, according to some embodiments. During visual inspection of the uterine tissues, the device 100 is rotated about its longitudinal axis by the doctor or medical professional. The position of the cannula 102 when rotated 180 degrees, is shown by the dotted outline 1810. The field of view (FOV) of the camera module in this example is shown which combined with the bending of the shaft 122 by and angle a, results in an effective field of view in the case of FIG. 18A of β. In the case of FIG. 18B, the camera is tilted upwards by an angle of γ, which results in an increase in effective field of view by twice γ, due to the rotation of the device. The effective field of view of the device 100 in FIG. 18B is shown as β2.

Figure 19:
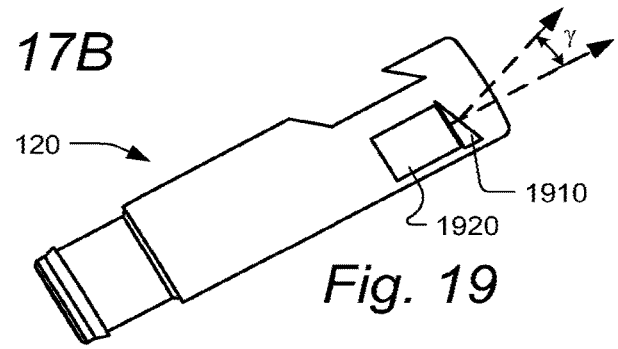
FIG. 19 shows a distal tip of a device for combined hysteroscopy and endometrial biopsy having a prism-aided tilted camera view, according to some embodiments.

FIG. 19 shows a distal tip of a device for combined hysteroscopy and endometrial biopsy having a prism-aided tilted camera view, according to some embodiments. In this case a prism 1910 is used to modify the angle of the camera module 1920 to provide an effective upwards tilting of the field of view of the camera module 1920 by an angle γ, which will result in an increased effective field of view of the device during use by two times γ.

Figure 20A:
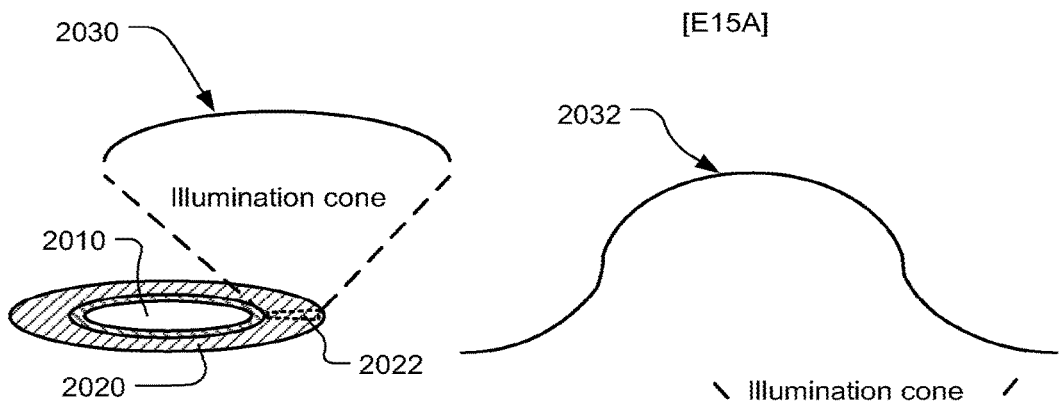
FIGS. 20A-20B and 21A-21B show examples of ring-type LEDs for use with a hysteroscopy device, according to some embodiments.
Figure 20B:
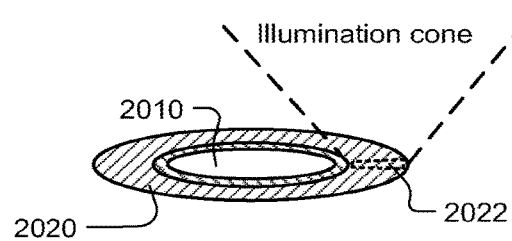
Figure 21A:
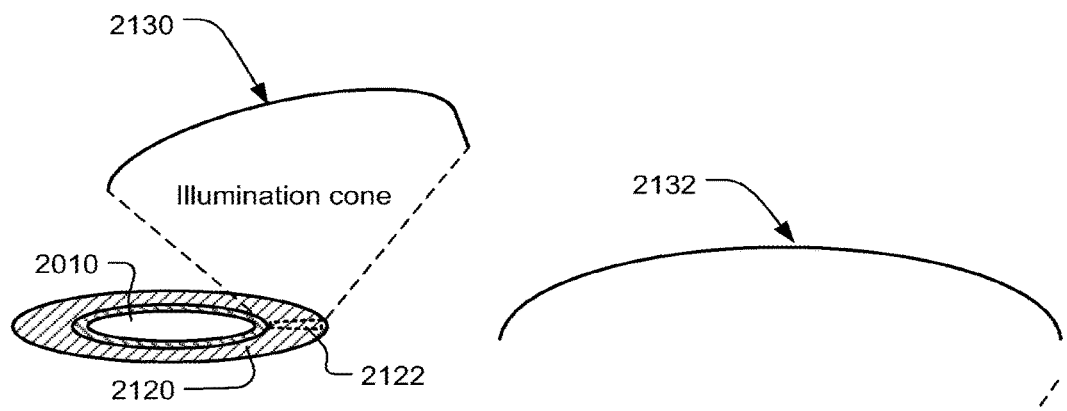
Figure 21B:
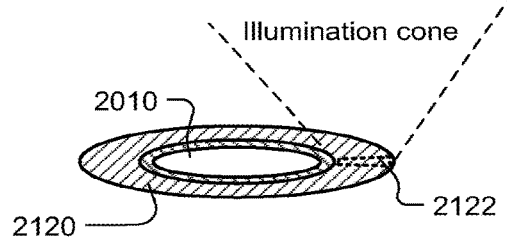

FIGS. 20A-20B and 21A-21B show examples of ring-type LEDs for use with a hysteroscopy device, according to some embodiments. In FIGS. 20A and 20B, a ring-type LED 2020 is shown surrounding a camera module 2010 that is used on the distal tip of a hysteroscopy device, such as device 100 described herein. In FIG. 20A, the illumination intensity distribution curve 2030 represents illumination from a single LED sector 2022 from ring LED 2020. In FIG. 20B, the overall illumination distribution curve 2032 represents the illumination from the entire ring LED 2020. Note that the center is much brighter than the edges, which may be problematic for imaging under some circumstances. According to some embodiments, a more evenly distributed intensity is achieved using an ring-type LED as shown in FIGS. 21A and 21B. In FIG. 21A, the ring type LED 2120 is shown surrounding a camera module 2010 that is used on the distal tip of a hysteroscopy device, such as device 100 described herein. The illumination intensity distribution curve 2130 represents illumination from a single LED sector 2122 from ring LED 2120. Note that the intensity is unevenly distributed towards the outer edge of the ring. The intensity profile is adjusted, for example, by using different thicknesses or orientations of the LED. FIG. 21B shows the resulting overall intensity distribution 2132 from ring LED 2120 where the center is more even with the edges, which results in enhanced imaging quality.

Figure 22:
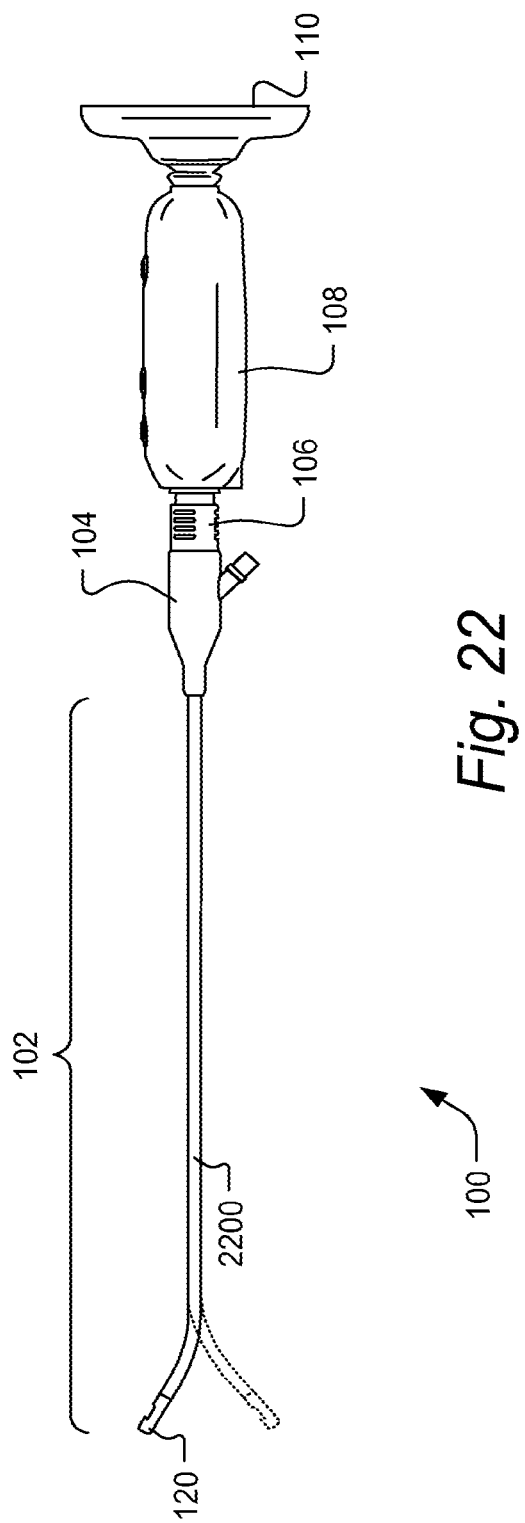
FIG. 22 shows a device for combined hysteroscopy and endometrial biopsy having malleable shaft, according to some embodiments.

FIG. 22 shows a device for combined hysteroscopy and endometrial biopsy having malleable shaft, according to some embodiments. In this example, cannula 102 includes a malleable shaft 2200. The shaft 2200 is malleable at the time of usage to aid reaching and visualizing recessed portions of the uterine cavity. The shaft 2200 can be made malleable, for example, by using a flexible nylon that includes one or more bendable metal wires running along the inside length of the shaft housing.

FIGS. 23 and 24 show details of a device for combined hysteroscopy and endometrial biopsy having separate tip and shaft assemblies, according to some embodiments. The cannula 102 of device 100 is made up of a tip 120 and a shaft 122. The tip 120 includes a molded acrylic tip housing 600 that houses the camera module, LEDs and other elements as described herein. The shaft 122 is made from extruded nylon, such as nylon 6, and may have internal structure such a shown in FIGS. 10, 26-28. According to some embodiments, shaft 122 can be made of another suitable material, such as Provista Copolymer. In FIG. 23 a video cable 2310 is also shown running along the inside of shaft 122 which carries video signals as well as control signals for the camera module and/or the LEDs in the tip 120. FIG. 24 shows how the tip assembly 120 is attached to the shaft 122. According to some embodiments, about 5 mm or more of the tip 120 is inserted into the shaft 122. If there are internal structures such as shown in FIGS. 10, and 26-28, they are spaced inwardly from the distal end of the shaft 122 so that proper mating can be achieved. Through the implementation of separately manufactured tip and shaft pieces, as shown, it has been found that the manufacturing cost can be decreased, and yield can be increased because the shaft is extruded while the acrylic tube is molded to provide sophisticated structure. Furthermore, the separate tip and shaft design allows for greater flexibility in forming the internal structures within both the tip and shaft.

Figure 25:
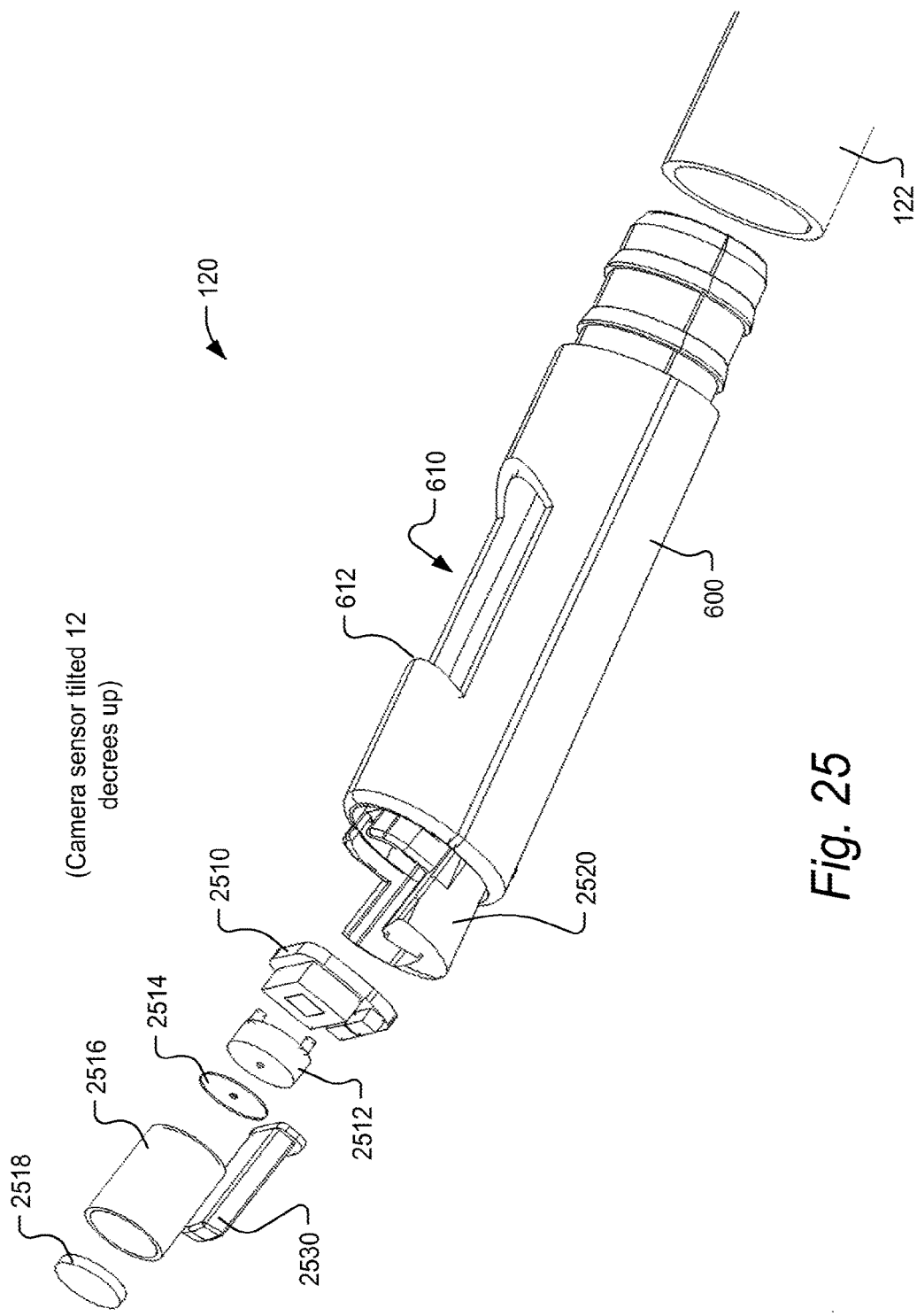
FIG. 25 is an exploded view of some internal components of a distal tip of a device for combined hysteroscopy and endometrial biopsy, according to some embodiments.

FIG. 25 is an exploded view of some internal components of a distal tip of a device for combined hysteroscopy and endometrial biopsy, according to some embodiments. In this example, tip assembly 120 is shown with various parts of the camera module separated for ease of viewing. The camera module includes CMOS sensor module 2510, lens 2512, iris 2514, shield 2516 and glass cover 2518. The CMOS sensor module 2510 includes a low voltage color CMOS image sensor core, image sensor processing and image output interface circuitry on a single chip such as the OmniVision 7675. By providing integrated digital video processing within sensor module 2510, all video processing can be performed directly on the same PCB as the CMOS sensor, or on the same substrate in which the CMOS is formed such that the imaging plane of the CMOS and the plane along which the video processing circuits extend substantially coincide. In this example, the video signal from sensor module 2510 can be in any suitable video format, such as NTSC, PAL, or another common video format, so that no further video processing would be required to drive widely available displays for common video formats such as TV displays, tablets, computers and hospital workstations. Also shown in FIG. 25 are one or more LEDs 2530. According to some embodiments another LED can be used mounted above the camera module. The holder 2520 retains the camera module and LEDs. According to some embodiments, the holder 2520 holds the camera module at an up-tilted angle of for example 12 degrees from the longitudinal axis of the tip housing 600.

Figure 26:
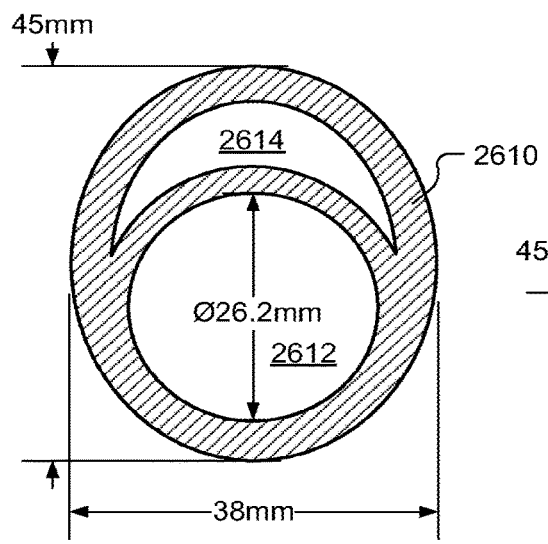
FIGS. 26-28 are cross sections showing examples of different internal shaft structures within a cannula for a device for combined hysteroscopy and endometrial biopsy, according to some embodiments.
Figure 27:
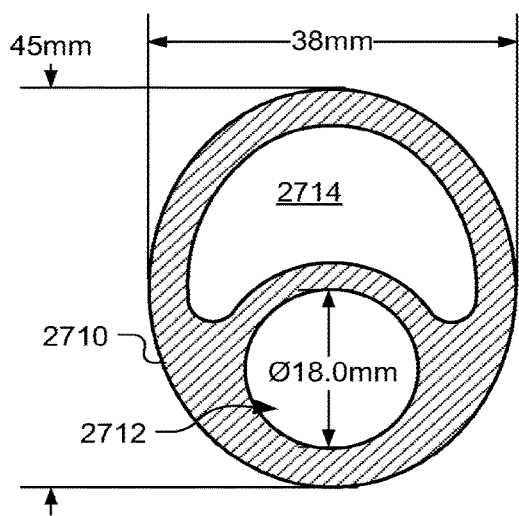
Figure 28:
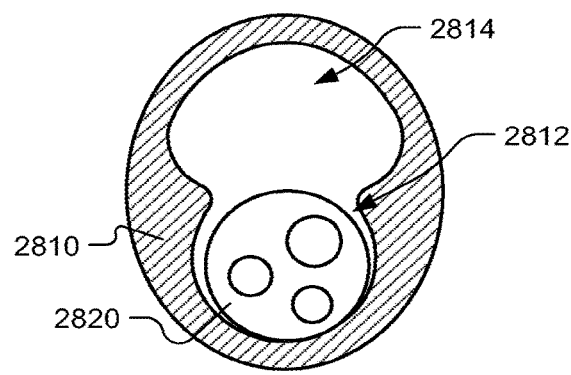

FIGS. 26-28 are cross sections showing examples of different internal shaft structures within a cannula for a device for combined hysteroscopy and endometrial biopsy, according to some embodiments. In FIG. 26, shaft 2610 includes a separate channel 2612 for the cable used for video and control signals as well as LED power. The upper channel 2614 is used for as the fluid channel for both in-flow and out-flow directions. Similarly, in FIG. 27, shaft 2710 includes a separate channel 2712 for the cable, while an upper channel 2714 is used for as the fluid channel for both in-flow and out-flow directions. In the example of FIG. 28, a partially separated internal structure is used. The shaft 2810 includes an upper lobe 2814 used for fluid flow and a lower lobe 2812 that primarily holds the cable 2820 used for LED power, video signals and control signals for the camera. The structure of FIG. 28 allows for simplified assembly since it is easier to position the cable 2810 in the lower lobe than to thread or fish it through a separate channel.

FIGS. 29 and 30 show further details of a distal tip for a device for combined hysteroscopy and endometrial biopsy, according to some embodiments. FIG. 29 is a perspective view of the distal tip 120 and distal end of shaft 122, according to some embodiments. As in some other described embodiments, the tip 120 includes a tip housing body 600 that is made from molded acrylic, for example a single molded piece of transparent acrylic. The tip 120 includes a side facing sampling port 610 and front facing fluid port 2940. A forward facing camera module includes a glass cover 1712 and in this case an acrylic camera module housing shell 2910. Two forward facing LEDs 2920 and 2922 are positioned just below the glass cover 1712. The cable 1612 used for LED power, video signals and control signals for the camera is also shown running down the shaft 122. FIG. 30 is a cross section of the tip and shaft shown in FIG. 29.

Conventional endoscopes are typically tethered and cumbersome to use. They require skilled staff to operate and maintain. This makes it especially difficult in time critical locations such as an emergency room, operating room, and other areas of a medical facility where multiple devices and instruments are being used simultaneously. According to some embodiments, the device 100 shown for example in FIGS. 1-5 is a hand-held, compact single use endoscope. In these cases, endoscope 100 is provided in a sterile package, so is ready for immediate use without requiring any preparation for diagnostic or therapeutic procedures. According to some embodiments the single use device 100 needs no sophisticated connectors such that the entire endoscope is supplied in a sterile package ready for use.

Figure 31:
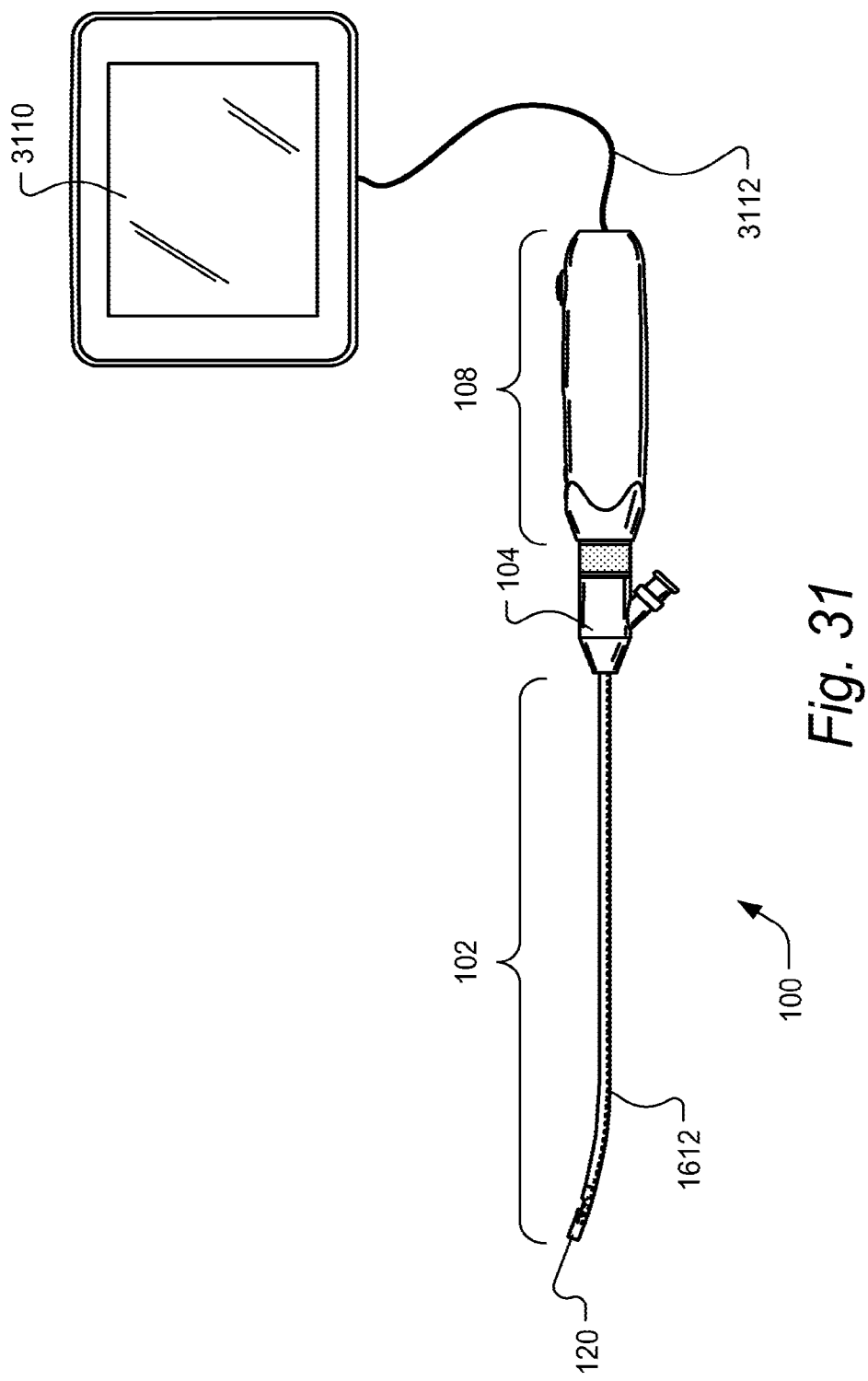

FIGS. 31-33 show a single-use device for combined hysteroscopy and endometrial biopsy, according to various embodiments. In the case of FIG. 31, device 100 includes an external monitor 3110 for viewing the images and/or video. A sterile cord 3112, which transmit the images and video to the external monitor, is attached to and is packaged with the device 100.

In the case of device 100 of FIG. 32, the images and video are transmitted by a wireless connection. The handle 100 includes a wireless transmitter 3212 and the eternal monitor 3210 includes a wireless receiver. According to some embodiments Wi-Fi technology is used. According to some embodiments, a device such as a smart phone 3220, a tablet computer 3222, a mobile computer, or other mobile device having wireless and display capabilities are used to view the images and/or video.

In the case of FIG. 33, the device 100 includes a gyroscopic module 3310 embedded to provide constant reference of orientation. A video processor is used to register the displayed images upright on the devices such as devices 3210, 3110, 3220 and 3222.

Figure 34:
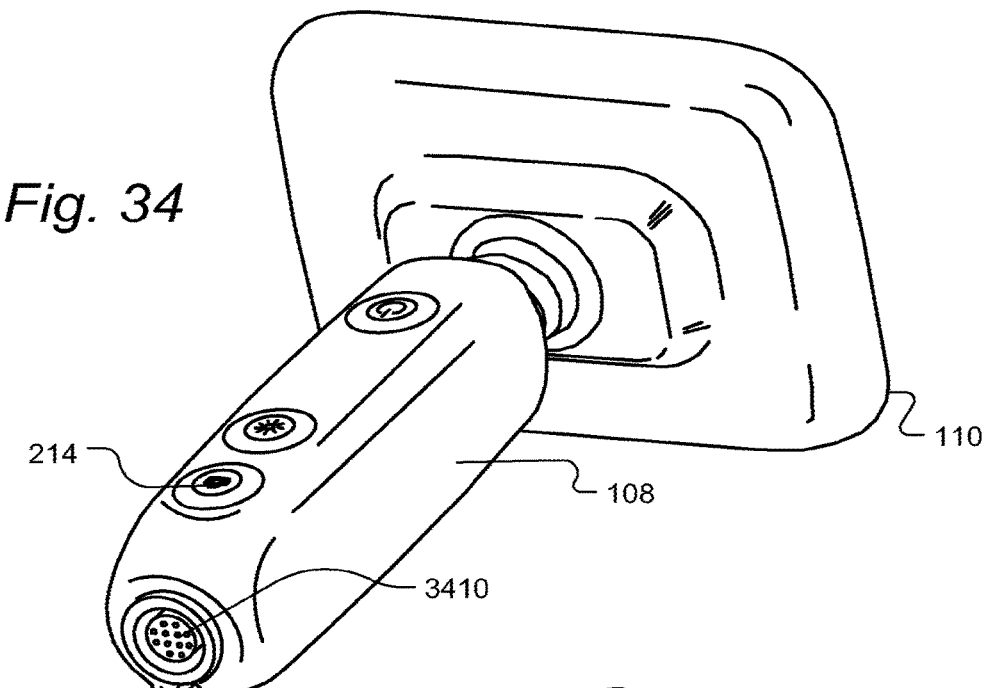
FIGS. 34-39 show a device combined hysteroscopy and endometrial biopsy having a detachable handle, which can be mated with a docking station, according to some embodiments.
Figure 35:
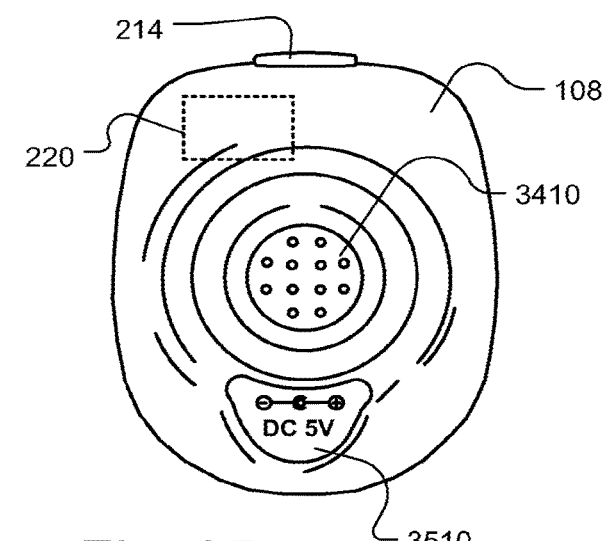

FIGS. 34-39 show a device for combined hysteroscopy and endometrial biopsy having a detachable handle, which can be mated with a docking station, according to some embodiments. FIGS. 34 and 35 show details of the handle and display detached from the fluid hub and cannula, according to some embodiments. FIG. 34 is a perspective view wherein handle 108 and display 110 are detached from the sliding connector 106 of the fluid hub 104 such as shown in FIG. 1. The distal end of the handle body 108 includes connector 3410 that has pin sockets that are used both for communicating and supplying power to the cannula when connected as well as to transmit video and control signals and settings to and from a base station or docking station when docked. The handle 108 also includes a recessed DC connector 3412 that is used to supplying power to the handle 108 when docked, for example to recharge the battery 220 and/or to prevent battery drain when downloading or viewing images and video and/or uploading settings to the unit. FIG. 35 is a distal end view of the handle 108, and shows the rubber flap 3510 that seals the DC power connector 3412 when not being used such as during docking with a docking station.

Figure 38:
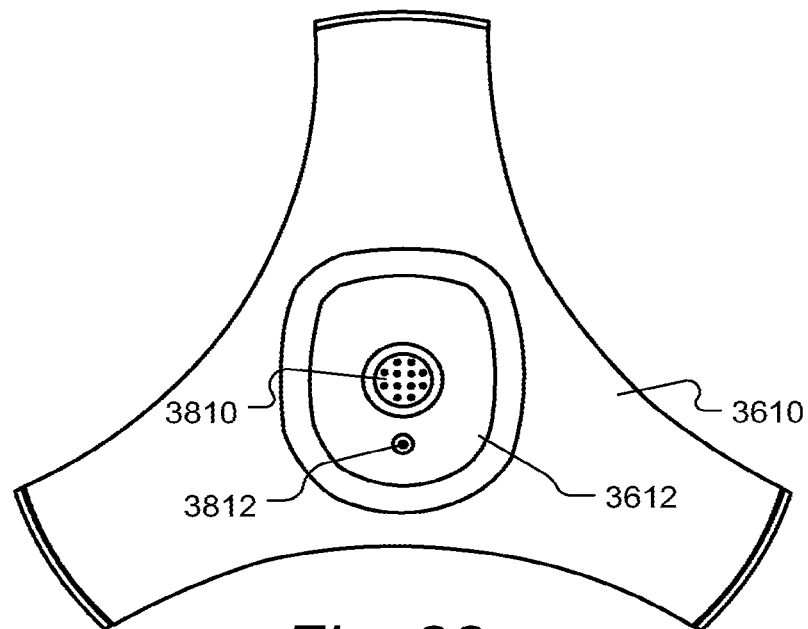
Figure 39:
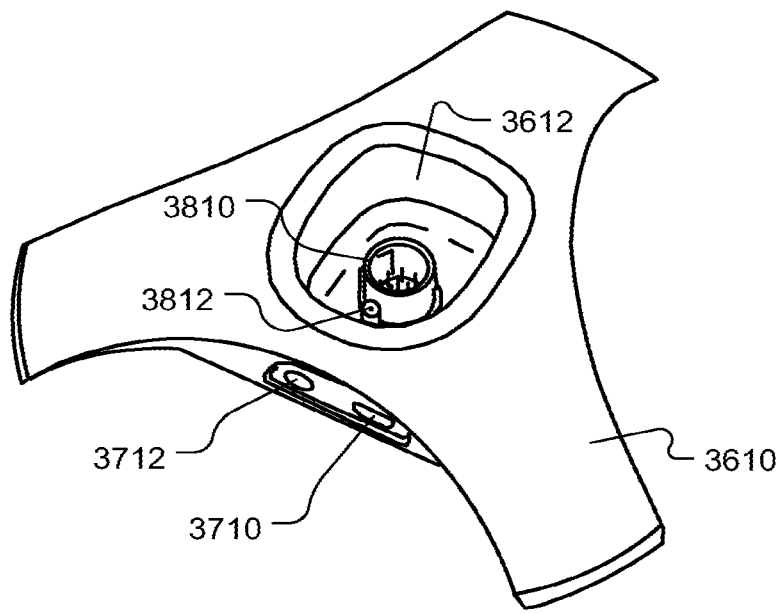

FIGS. 36 and 37 are a perspective view and a side view, respectively, of the handle and display docked to a base station, according to some embodiments. The handle 108 and display 110 are shown mated, or docked with base station 3610. The distal portion of the handle 108 is inserted into the opening, lined with a rubber liner 3612. When inserted in the base station 3610, the handle and display are well supported protected as shown. In addition to providing a stable base for the handle and display, the base station 3610 can also be used to supply power to handle and display, such as for recharging the battery and/or for viewing images and video on the display 110. For this purpose, an external power supply can be connected to the base station 3610 via the DC power connector 3712. The base station can also be used to communicate with the handle and display, such as to view and or download images or video, as well as to view and modify settings. The mini-USB connector 3710 can be used for this purpose, as well as to supply power to the base station (as well as to the handle and display when docked). According to some embodiments, the base station 3612 includes wireless communication circuitry, such as Wi-Fi, for communicating with devices such as a smart phone 3220, a tablet computer 3222 (as shown in FIG. 32), a mobile computer, or other mobile device having wireless and display capabilities are used to view the images and/or video. FIGS. 38 and 39 are a plan view and perspective view of the base station 3610 without the handle inserted. As can be seen a mating connector 3810 is provided which mates with the connector 3410 as shown in FIGS. 34 and 35. Also provided is a DC power connector 3812 that mates with the DC power connector 3412 as shown in FIG. 34. Additional storage and/or processing can be provided for still or video images from the device 100, such as storage in PACS or other archival storage systems of the type commonly used in hospitals and clinics for patient records and medical images and/or processing in work stations commonly used for processing and viewing of medical images in hospitals and clinics. The still and/or video images from the device 100 can be formatted as needed for a commonly used format, such as DICOM in one example, in the base station 3610, or one or more of the devices 3220 and 3222, or a mobile computer, or a computing device connected to the base station 3610. The formatted still and/or video images then can be transmitted in accordance with the selected format to a PACS or other storage system, and/or to a workstation where they can be further processed as is known in the art, e.g., to enhance certain aspects of images or to carry out CAD (computer aided detection) processes, and can be displayed alone or together with images from other modalities or prior images of the same patient for diagnostic or other purposes. According to some embodiments the base station as shown in FIGS. 36-39 are particularly useful when the cannula 102, fluid hub 104 and connector 106 are intended to be disposed of after a single-use, while the handle 108 and display 110 are designed to be reused many times. In this case the handle and display are conveniently stored on the base station while a supply of single-use cannula/hub assemblies are kept in pre-sterilized packages ready for use.

Figure 40:
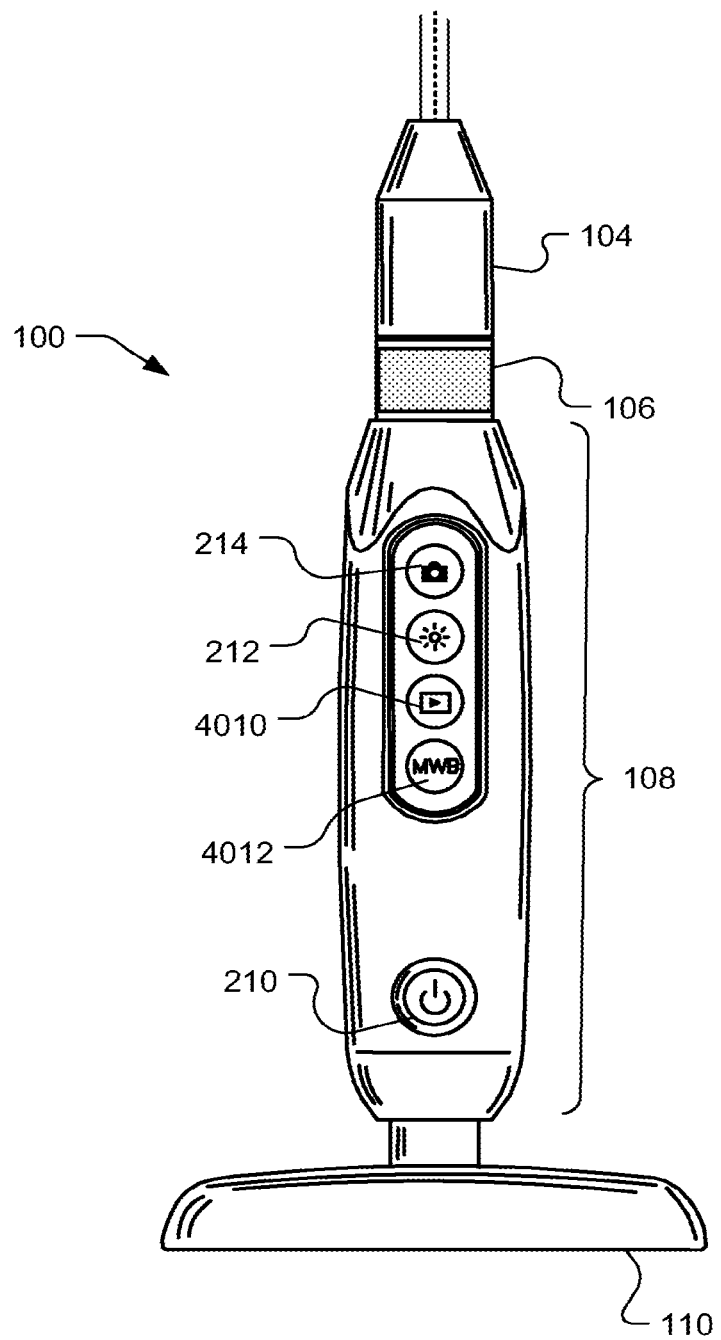
FIG. 40 is a top view of a device for combined hysteroscopy and endometrial biopsy having additional buttons on the handle, according to some embodiments.

FIG. 40 is a top view of a device for combined hysteroscopy and endometrial biopsy having additional buttons on the handle, according to some embodiments. As shown, in addition to the ON/OFF button 210, LED brightness control button 212, and Snap/Video button 214 as described in FIG. 2, the handle 108 includes a playback button 4010 and a manual white balance button 4012. The playback button 4010 is used to replay snapshots and/or video taken during the procedure such that medical personnel can later review the images or video on the display 110. The manual white balance button 4012 is used to cycle through several pre-set white balance levels so that the user can quickly and easily select a suitable white balance for the particular case.

FIG. 41 shows a display screen user interface for a device for combined hysteroscopy and endometrial biopsy, according to some embodiments. The touch-screen display 110 of hysteroscopy device 100 is shown with home screen 4110. According to some embodiments, the display is 3.5 inches in size. The home screen 4110 includes four options that can be selected by a user by touching the screen. A battery status icon 4120 is shown in the upper left corner. The home screen 4110 includes four user-selectable menu options (or soft-buttons) that are labeled as shown: new patient, preview, playback and setup. According to some embodiments, pressing the power ON/OFF button 210 for 1 second or less is used as a "home button" on the device 100 such that the home screen 4110 is displayed.

Figure 42:
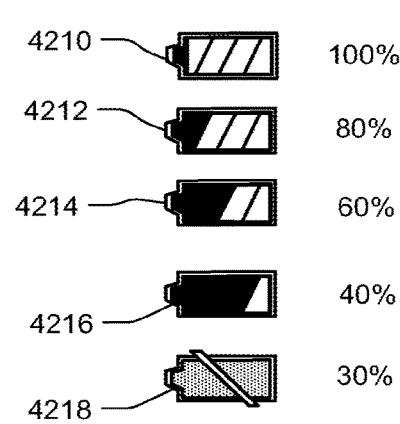
FIG. 42 shows details of some elements of a user interface for a hysteroscopy device, according to some embodiments.

FIG. 42 shows details of some elements of a user interface for a device for combined hysteroscopy and endometrial biopsy, according to some embodiments. Five levels of battery status can be displayed to the user in these examples on a display associated with the device, such as display 110. Icons 4210, 4212, 4214, 4216 and 4218 are used for 100%, 80%, 60%, 40% and 30% capacity remaining in rechargeable battery 220 respectively. According to some embodiments, a red color and/or flashing is used for the icon 4218 to further draw the attention of the user.

Figure 43:
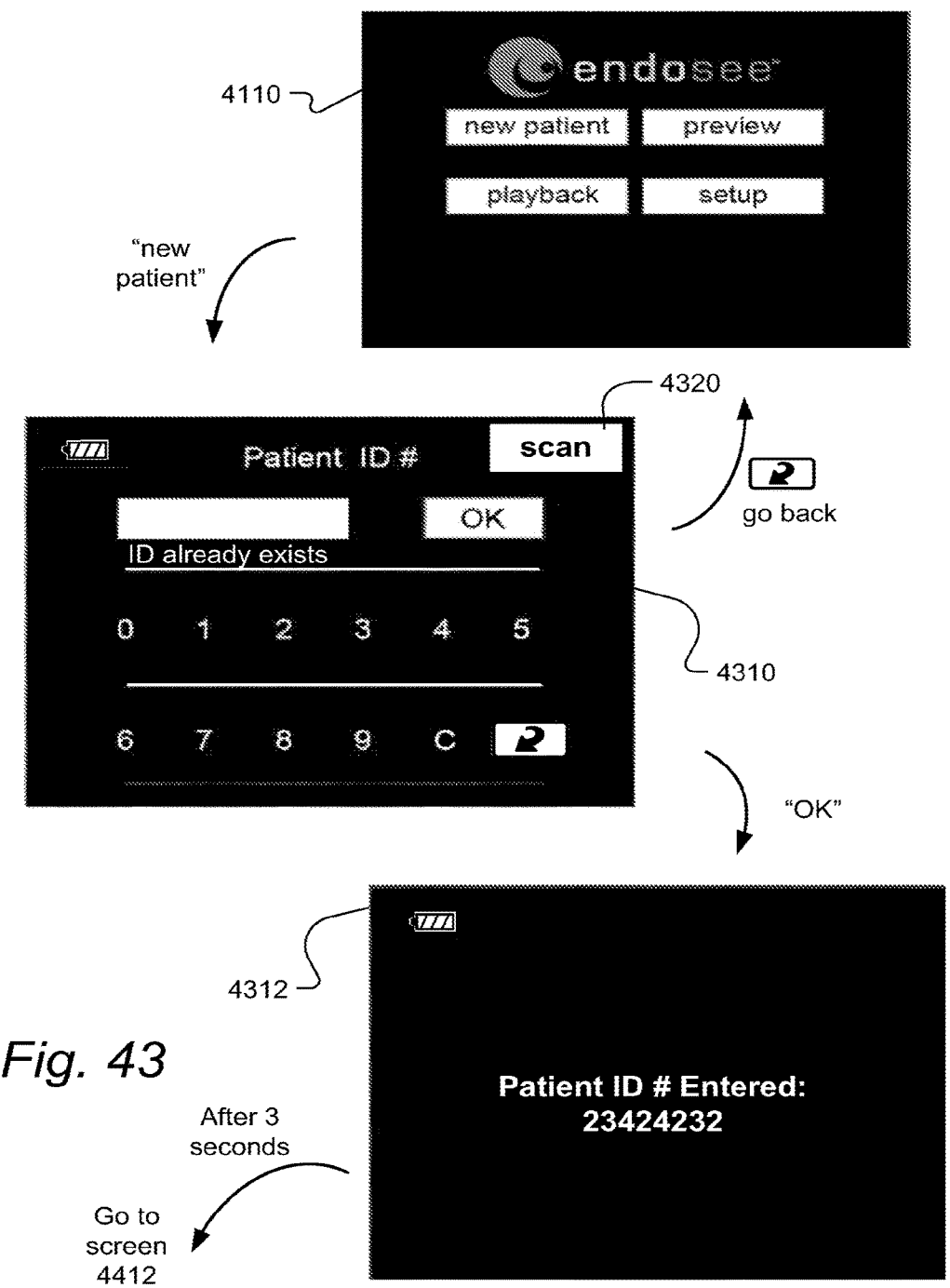
FIG. 43 is a flow chart showing aspects of a user interface for a hysteroscopy device relating to entering new patient information, according to some embodiments.

FIG. 43 is a flow chart showing aspects of a user interface for a device for combined hysteroscopy and endometrial biopsy relating to entering new patient information, according to some embodiments. From home screen 4110 on a display such as 110, when the user selects "new patient" screen 4310 is displayed, allowing the user to enter a new patient ID number. After entering the new number using the number buttons provided (e.g., a soft button), pressing "OK" confirms the user's entry. If the ID already exists, the message "ID already exists" is displayed prompting the user to enter a different number. A "go-back" button is also provided in the lower right corner, and in many other screens shown herein, that allows the user to return to the previous screen. According to some embodiments, the camera module on the distal tip of the device 100 can be used to enter patient information as a barcode scanner for barcodes and/or matrix barcodes such as a QR Code, which may already be on the patient's file or paperwork, to quickly and accurately enter a patient ID number. In this case a "scan" button 4320 is included on screen 4310. After successfully entering a new patient ID number, the confirmation screen 4312 is displayed for a fixed duration, for example 3 seconds, after which a transition is automatically made to the preview screen 4412 in FIG. 44 infra, such that live video from the camera module of device 100 is displayed.

Figure 44:
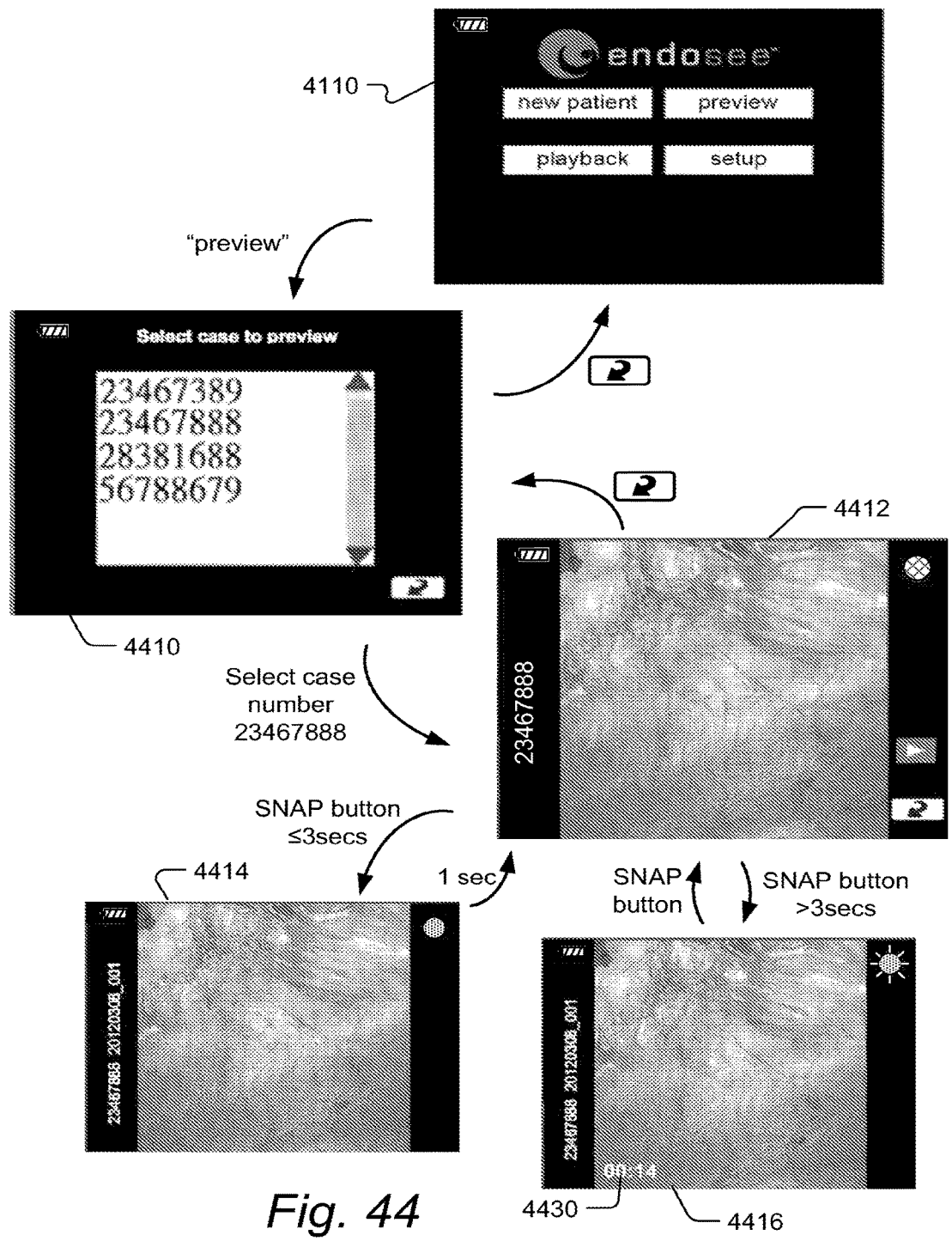
FIG. 44 is a flow chart showing aspects of a user interface for a hysteroscopy device relating to previewing images and video, according to some embodiments.

FIG. 44 is a flow chart showing aspects of a user interface for a device for combined hysteroscopy and endometrial biopsy relating to previewing images and video, according to some embodiments. From home screen 4110 on a display such as 110, when the user selects "preview" screen 4410 is displayed, allowing the user to select from among a list of cases, or patients, to use. Touching directly on one of the numbers highlights the number, such with yellow highlighting. Touching the up and down arrows on the scroll bar on the right side scrolls through the list (or scrolls the colored highlight field through the list). According to some embodiments touch and drag gestures such as is known with smartphone and tablet computer interfaces can be used for scrolling through lists of numbers or images. When a highlighted number is pressed again, then screen 4412 is displayed, in which live video from the distal mounted camera of device 100 is shown to the user. The live preview screen 4412 also includes the patient ID number on the left side as well as a green disk icon in the upper right corner to indicate to the user that live preview is being displayed. Pressing the go-back button returns to the previous screen. A playback button on the right side allows the user to re-play a predetermined length of video, such as 3-5 seconds. Pressing the snap button 214 for 3 seconds or less causes capture of a single photo, as shown in screen 4412. A solid red disk icon is displayed in the upper right corner. The single capture image is displayed for 1 second (or other fixed length of time) after which the live preview screen 4412 is returned to. Additionally, or in addition to displaying the image, an audible photo shutter sound can be played and/or a brief transition to white or black can be used to indicate to the user that a still image has been captured, according to some embodiments. If the snap button 214 is pressed for longer than 3 seconds, video is captured, as shown in screen 4416. In this case the video being captured is displayed while the red disk icon in the upper right corner blinks to indicate that video is being captured. Video capture begins and continues until the snap button is pressed again. According to some embodiments a timer 4430 can also be provided showing the length of video captured.

Figure 45A:
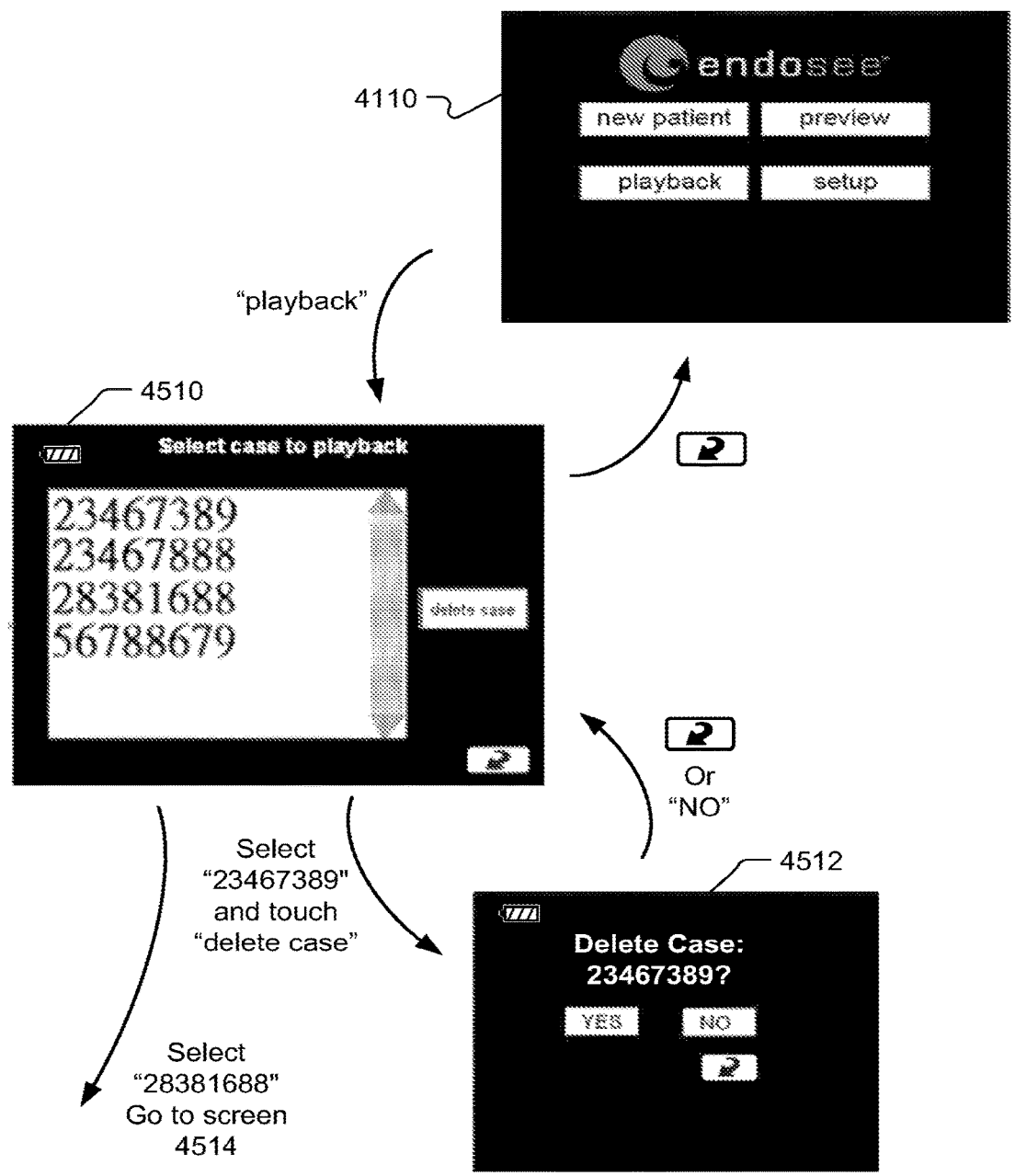
FIGS. 45A-45B are a flow chart showing aspects of a user interface for a hysteroscopy device relating to playback of saved images and video, according to some embodiments.
Figure 45B:
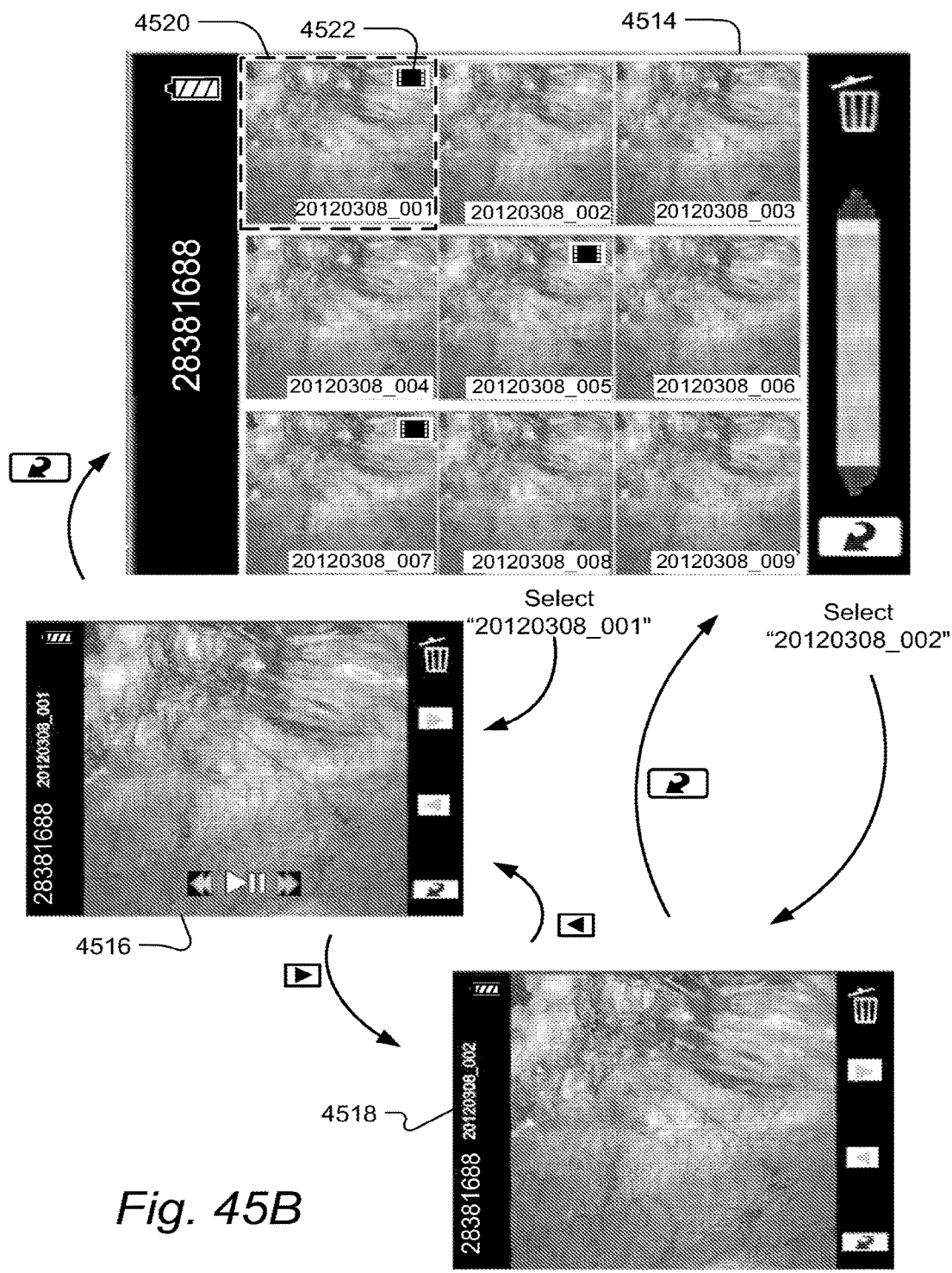

FIGS. 45A-45B are a flow chart showing aspects of a user interface for a device for combined hysteroscopy and endometrial biopsy relating to playback of saved images and video, according to some embodiments. In FIG. 45A, from home screen 4110 on a display such as 110, when the user selects "playback" screen 4510 is displayed, allowing the user to select from among a list of cases, or patients, to playback. As in screen 4410, yellow highlighting is used to first select a case. If the user selects "delete case" then the highlighted case will be deleted after a confirmation screen 4512. If a case is highlighted and then selected, screen 4514 in FIG. 45B is displayed. Screen 4514 includes thumbnail images of all of the captured still images and video, which can be scrolled through (using the scroll bar, or using a swipe gesture). A particular image or video is highlighted, such as will yellow, as indicated by the dashed line 4520. The thumbnail images include the file number, as well as a movie icon 4522 when the file is video rather than a still image. Screen 4514 also shows the patient ID on the left margin, as well as a delete icon and go back button on the right margin. The delete icon can be used to delete an individual highlighted file, after user confirmation. Selecting a highlighted video file, such as image "20120308_001" caused playback screen 4516 to be displayed. The user can control the video playback using the play/pause, rewind and fast forward buttons. The user can also move to the next or previous file using the arrow buttons in the right margin. Screen 4518 shows an example of displaying a still image.

Figure 46:
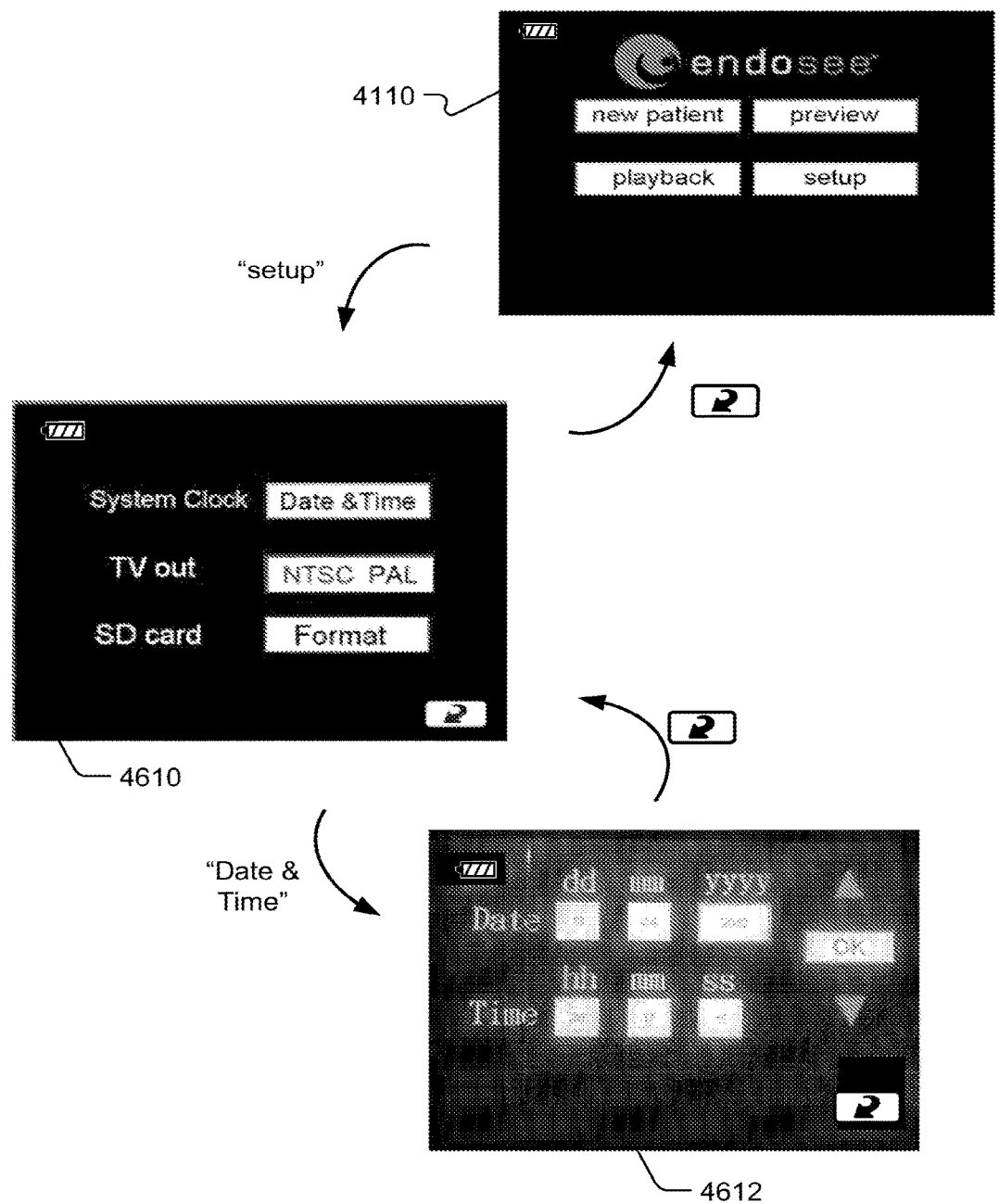
FIG. 46 is a flow chart showing aspects of a user interface for a hysteroscopy device relating to settings, according to some embodiments.

FIG. 46 is a flow chart showing aspects of a user interface for a device for combined hysteroscopy and endometrial biopsy relating to settings, according to some embodiments. From home screen 4110 on a display such as 110, when the user selects "setup" screen 4610 is displayed, allowing the user to view and modify various device settings. Examples of such settings are the system clock, which can be modified using the screen 4612, as well as the TV out format and formatting the internal flash memory card. According to some embodiments, many other settings can be programmed by the user using the interface shown.

FIGS. 47-48 are side views showing details of the shapes of distal tips of a device for combined hysteroscopy and endometrial biopsy, according to some embodiments. It has been found that the distal tip of the device preferably should be rounded for several reasons. First, the tip roundness greatly lowers the risk of accidental damage to the uterus, such as piercing or puncturing delicate uterine tissues during use. Secondly, the distal tip roundness affects the resistance of the distal tip to collecting matter that can clog the tip and blocking the view of the camera. It has been found that the edges of the tip should preferably be rounded by at least a radius of 0.25 mm. In the example shown in tip 120 of FIG. 47, the edges of the distal tip such as shown in region 4702 are rounded to a radius of 0.5 mm. Additionally, it has been found that there is benefit to the front face of the distal tip to be rounded as well. By making the front face 4710 convex the tip is much less likely to collect tissue debris or other matter that might occlude the field of view or make it more difficult to obtain clear images from the camera module. In the example of FIG. 47, the front face 4710 is preferably rounded to a radius of about 10 mm. In the example of FIG. 48, the distal tip 120 preferably has a substantially flat central portion 4810, surrounded by an outer region 4812 that is rounded to a radius of about 2.5 mm. The edge portion 4802 is rounded to a radius of about 0.44 mm. It has been found that making substantially flat the central portion 4810 (which is less than about 30% of the total frontal area in this example) can be useful in reducing distortion in the images captured by the camera module while the substantial curved portions 4812 and 4802 provide enough rounding to avoid tissue collection and reduce tissue damage risks. According to some embodiments, it has been found that the outer region making up at least 50% of the frontal area should be substantially rounded.

Figure 49:
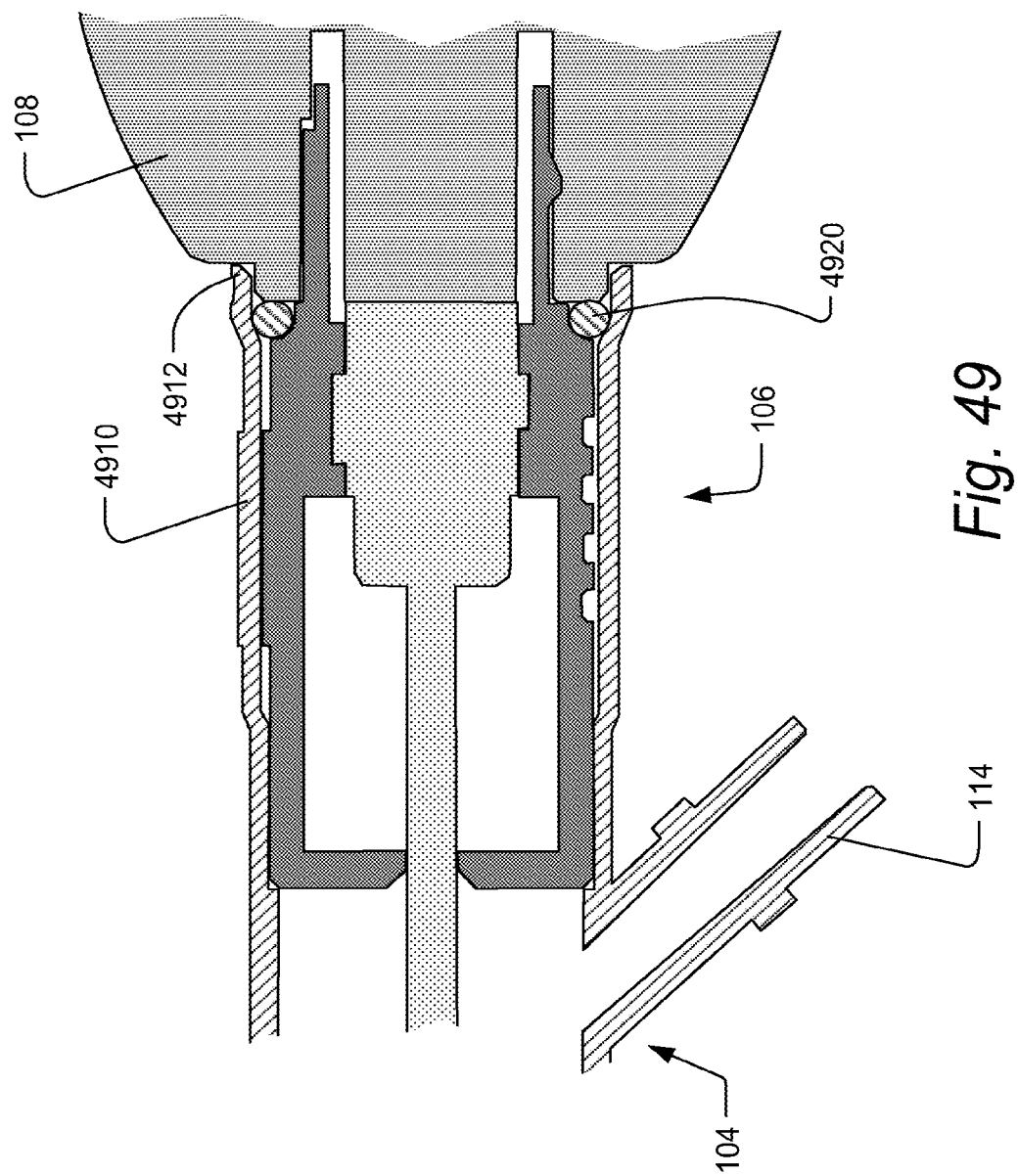
FIGS. 49-51 illustrate further details and embodiments.

FIG. 49 is a cross section showing details of a sealed sliding connector for a device for combined hysteroscopy and endometrial biopsy, according to some embodiments. The sliding connector 106 is shown here with an outer shell 4910 that includes a lip 4912 that fits over an o-ring seal 4920 and a portion of the handle assembly 108 so as to provide a suitable seal between the fluid hub 104 and the handle assembly 108. Multiple similar seals can be provided along the length of connector 106 to further isolate handle 108 from patient matter when the cannula assembly of the device is disposable but handle 108 is reusable. An additional connector (not shown) can be inserted between connector 106 and handle 108 for further insulation, and can be made in a way to allow the additional connector to be sterilized before used for another patient (as it only has to provide an electrical connection between the cannula and the handle).

Figure 50:
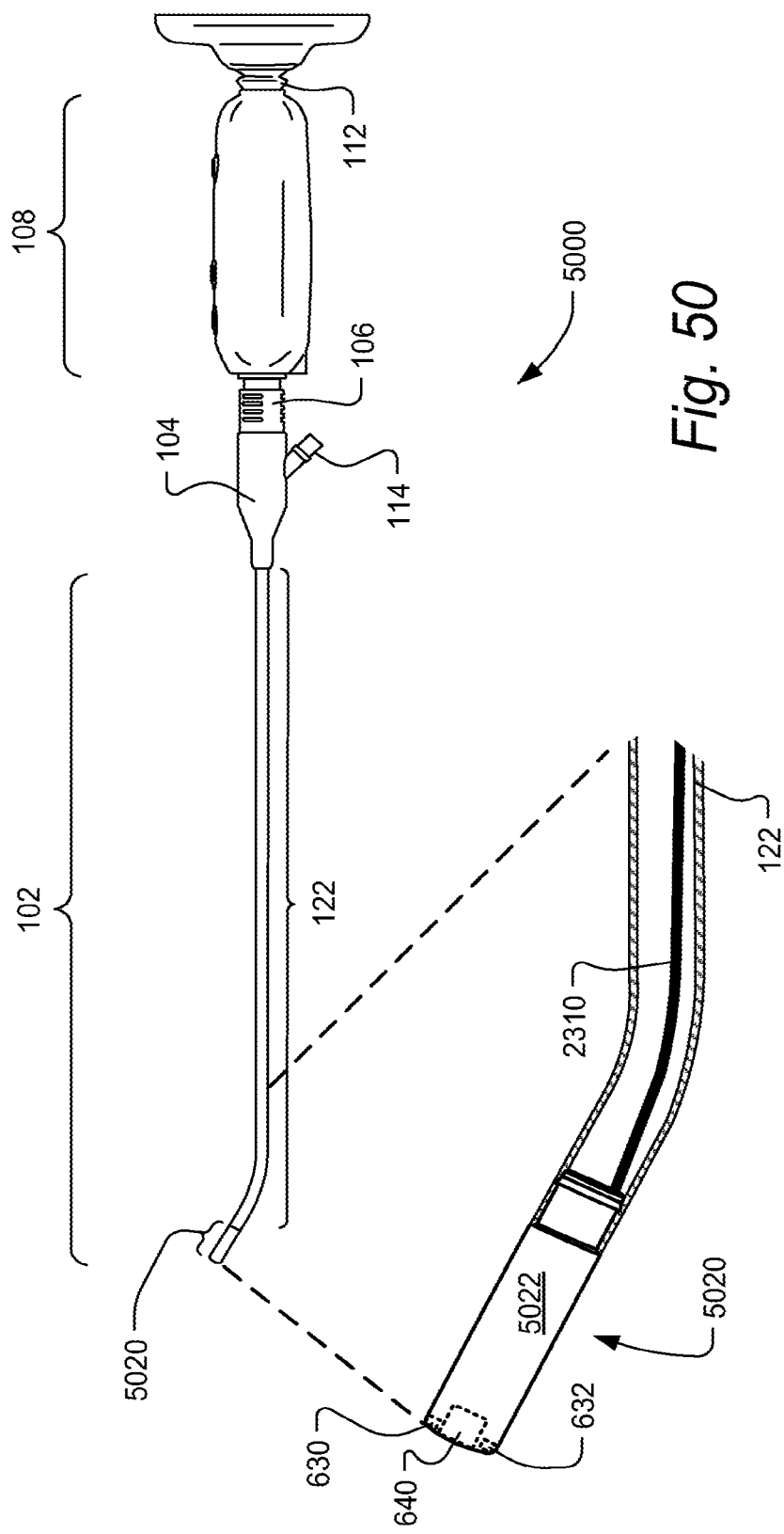

FIG. 50 shows a hysteroscope, according to some embodiments. The hysteroscope 5000 can be identical or similar to the device 100 described herein (including, for example, the user-interface described in FIGS. 41-46), except that it is intended only for hysteroscopy and not endometrial biopsy. As such the distal tip assembly 5020 does not have a side-facing sampling port and does not make use a separate fluid channel for sampling (as shown in FIGS. 8A-E and 9). However, a separate channel coupled to a side port or another forward facing port can be provided if desired to both deliver fluid to the uterus and withdraw fluid (and other matter) from the uterus, for example distend and relax the uterus or to flush the uterus. The assembly 5020 includes a tip body 5022, camera assembly 640 and LEDs 630 and 632. According to some embodiment, as with the device 100, the cannula 102 (including distal tip 5020), fluid hub 104 and sliding connector 106 are designed for a single-use, while the handle 108 and display 110 are designed to be re-used many times. Thus, the hysteroscope 5000 includes many of the same features and benefits from many of the same advantages as the combined hysteroscopy and biopsy device 100.

Figure 51:
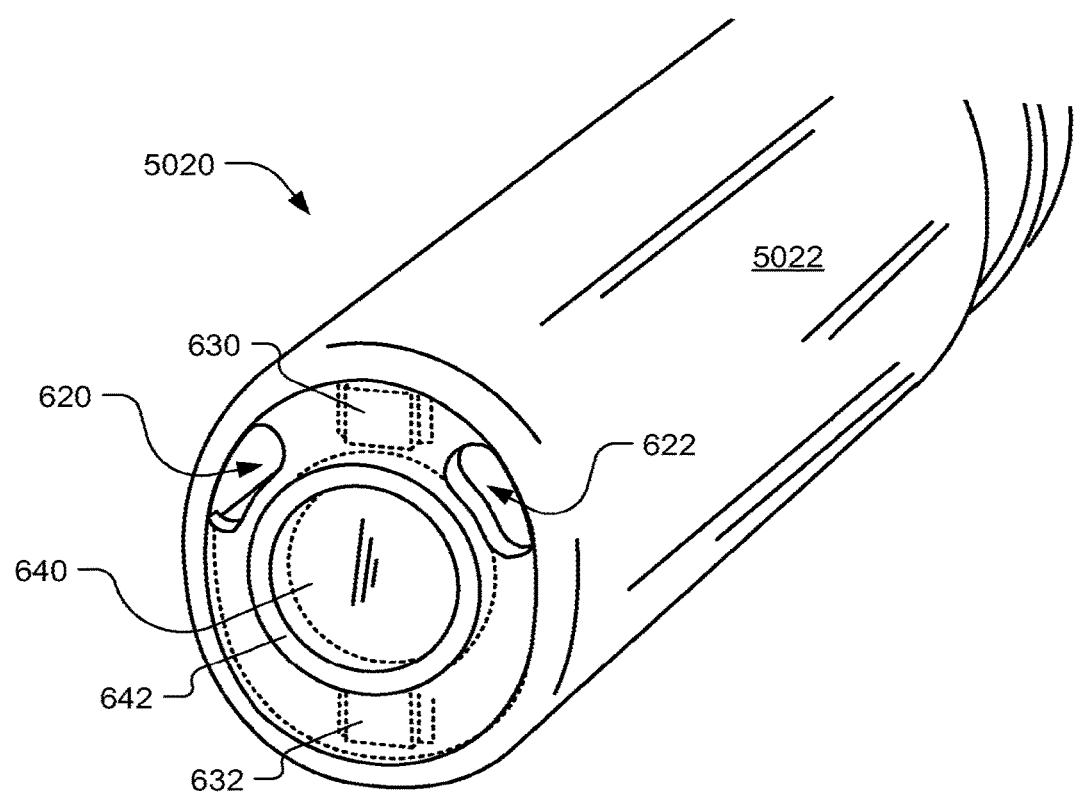

FIG. 51 shows details of a distal tip for a hysteroscope such as shown in FIG. 50. The distal tip assembly 5020 is shown with the tip body 5022 including two forward facing fluid ports 620 and 622, two LEDs 630 and 632, as well as camera assembly 640.

Figure 52:
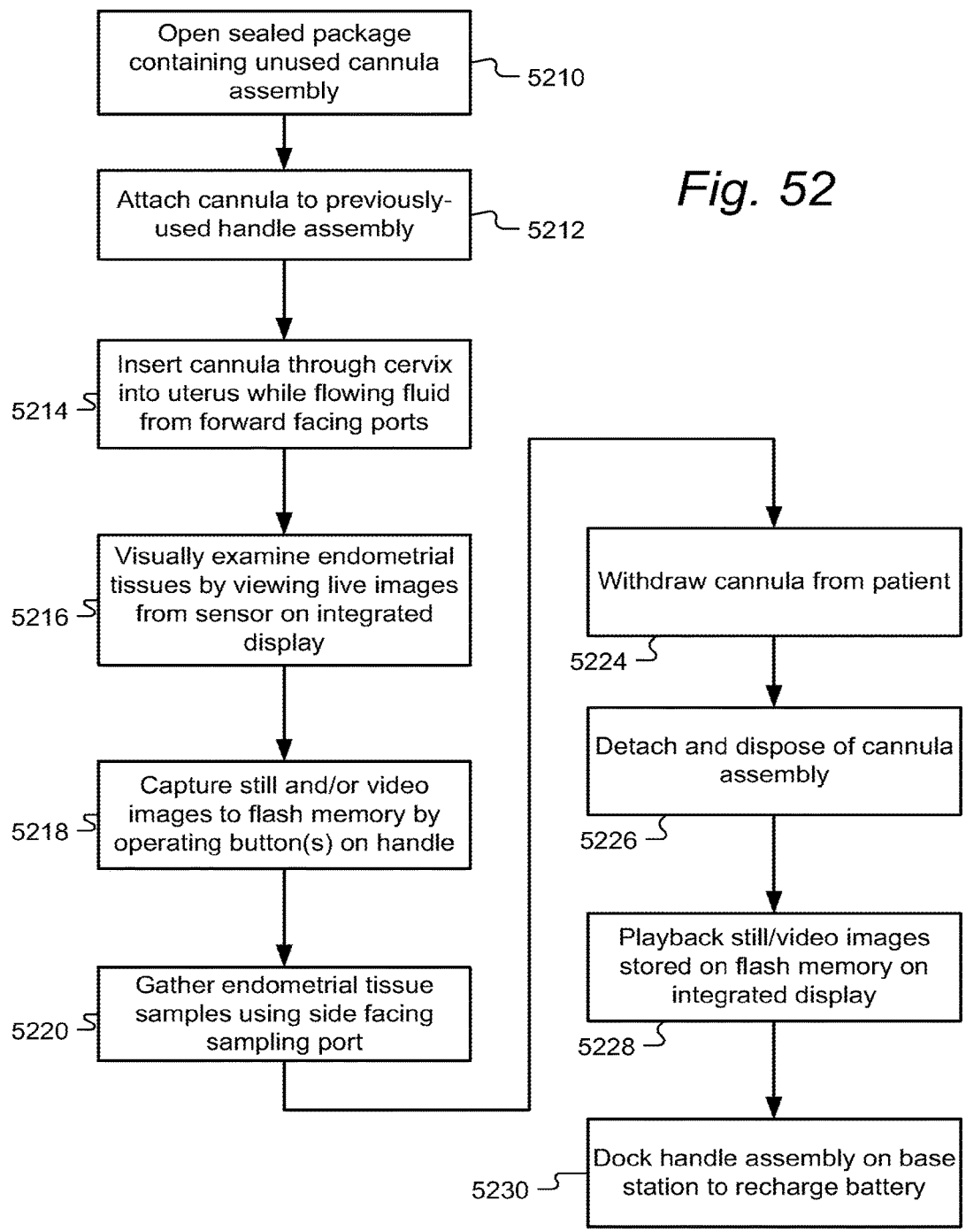
FIG. 52 is a flowchart illustrating examples of steps in using certain embodiments.

FIG. 52 is a flow chart illustrating an example use of a hysteroscopy device having the disposable cannula and re-usable handle and display, according to some embodiments. In step 5210, an unused cannula assembly, which for example includes cannula 102, fluid hub 104 and connector 106 as shown in FIG. 1 or in FIG. 50, is removed from a sterile package and in step 5212 the connector is attached to a previously used handle assembly, which for example includes a handle 108 and a display 110 as shown in FIG. 1 or in FIG. 50. Although the handle assembly has been previously used, it is cleaned and disinfected according to known standard practices, such as with rubbing alcohol or other disinfectant such as Cidex. Note that the example shown in FIG. 52 is for a previously used handle assembly, but the same steps would also apply to the case of a brand new handle assembly. In step 5214, the cannula is inserted through the cervix into the uterus, while flowing fluid from forward facing ports, such as ports 620 and 622 shown and described supra. Note that according to some embodiments, the sterile package is opened but not removed from the cannula assembly in step 5210. In this case the package is only opened the proximal end of the cannula, namely the end with the connector such that the connector can be attached to the handle. Then just prior to use, the remainder of the packaging is removed from the cannula. In step 5216 the user visually examines the endometrial tissue by viewing live images on the display 110. Lighting can be adjusted, for example using a control button on the handle. If the user wishes, still and/or video images can be captured using a control button on the handle. In step 5220, in the case where the device is for combined hysteroscopy and endometrial biopsy, tissues can be gathered using the side facing sampling port (such as port 610) without having to withdraw the cannula. In some cases steps 5216, 5218 and/or 5220 may be repeated as needed. Note that fluid induced distending and un-distending as described in some of the commonly assigned incorporated applications also is carried out to aid in examination and tissue collection, according to some embodiments. In step 5224 the cannula is withdrawn. In step 5226 the cannula assembly is disconnected, by detaching the connector from the handle, and the entire cannula assembly is disposed of. In step 5228 stored images are played back on the display, for example using a touch-screen interface as described supra. In step 5230 the handle assembly is docked to a base station for battery recharging and/or for transferring images and patient information out of the handle to other storage/processing facilities. According to some embodiments, a standard cleaning procedure is performed on the handle prior to docking on the base station. Note that the step 5228 of playing back the images can happen at any time after capturing in step 5218. For example, play back can be done before gathering samples, in step 5220, after withdrawal but prior to detaching the cannula in step 5226, or while the handle assembly is docked in the base station such that steps 5228 and 5230 are performed in parallel. In the case of viewing playback images while docked in a base station, tilting of display 110, as described with respect to FIG. 1, has been found to be useful in some situations.

Although the foregoing has been described in some detail for purposes of clarity, it will be apparent that certain changes and modifications may be made without departing from the principles thereof. It should be noted that there are many alternative ways of implementing both the processes and apparatuses described herein, including for using the described devices or certain aspects thereof for hysteroscopy but not for endometrial biopsy, or for endometrial biopsy but not for hysteroscopy, or for endoscopy and/or biopsy other than of the uterus. For example, in some applications the device shown in FIGS. 50-51 could also be used for taking fluid and/or fluid/tissue endometrial samples through the forward facing fluid parts. Accordingly, the present embodiments are to be considered as illustrative and not restrictive, and the body of work described herein is not to be limited to the details given herein, which may be modified within the scope and equivalents of the appended claims.

What is claimed is:

1. An endoscopic device, comprising:
   an elongate cannula configured for insertion through a cervix into a uterus;
   a camera assembly disposed adjacent a distal end of the elongate cannula for acquiring imagery of the uterus;
   a fluid port adjacent the distal end of the elongate cannula and through which fluid can flow to move debris away from the camera assembly to enhance the imagery acquired by the camera assembly;
   a handle disposed proximal to the elongate cannula;
   a display screen mounted to the handle;
   a memory configured to store instructions; and
   a processor configured to execute the instructions to perform operations comprising:
      processing the imagery acquired by the camera assembly to generate processed imagery of the uterus, and
      initiating presentation of one or more graphical user interfaces (GUIs) on the display screen, the one or more GUIs presenting the processed imagery of the uterus and one or more menus for collecting patient information via one or more soft buttons provided by the one or more menus, the one or more GUIs presenting the processed imagery of the uterus as a live video feed on the display screen automatically upon receipt of the patient information via the one or more soft buttons as the camera assembly continues to acquire additional imagery of the uterus, such that the live video feed provides live viewing of the uterus from the additional imagery,
   wherein the display screen is mounted to a proximal end of the handle such that the live video feed presented on the display screen automatically upon receipt of the patient information is viewable by a user of the endoscopic device while the endoscopic device is manipulated by the user.

2. The endoscopic device of claim 1, wherein the one or more GUIs present one or more input fields for receiving the patient information from a user to identify a patient.

3. The endoscopic device of claim 2, wherein the one or more GUIs present a message indicating that the patient information was previously received.

4. The endoscopic device of claim 2, wherein the one or more GUIs present an indication confirming receipt of the patient information.

5. The endoscopic device of claim 1, wherein the one or more GUIs present the processed imagery following user entry of the patient information.

6. The endoscopic device of claim 1, wherein the camera assembly is capable of scanning a machine-readable code for collecting the patient information to identify a patient such that the live video feed is presented on the display screen automatically upon receipt of the patient information via the machine-readable code.

7. The endoscopic device of claim 1, wherein the one or more soft buttons provide a list of one or more patient ID strings.

8. The endoscopic device of claim 7, wherein the live video feed is presented on the display screen automatically upon user selection of a patient ID string of the one or more patient ID strings.

9. The endoscopic device of claim 8, wherein the operations further comprise initiating a replay of a portion of the live video feed.

10. The endoscopic device of claim 8, wherein the operations further comprise initiating a capture of a portion for the live video feed.

11. The endoscopic device of claim 10, wherein the one or more GUIs present a timer indicating a duration of the portion of the live video feed.

12. The endoscopic device of claim 8, wherein the operations further comprise initiating a capture of a photo from the live video feed.

13. The endoscopic device of claim 1, wherein the operations further comprise initiating a replay of the processed imagery.

14. The endoscopic device of claim 13, wherein the one or more GUIs further present one or more thumbnail images representing all of the photos and videos captured in association with a patient identified by the patient information.

15. The endoscopic device of claim 14, wherein the one or more thumbnail images respectively present file names.

16. The endoscopic device of claim 14, wherein at least one thumbnail image is associated with a video.

17. The endoscopic device of claim 14, wherein the one or more GUIs comprise a video playback screen that is presented upon user selection of a thumbnail image of the one or more thumbnail images that represents a video.

18. The endoscopic device of claim 14, wherein the one or more GUIs comprise a still image screen that is presented upon user selection of a thumbnail image of the one or more thumbnail images that represents a photo.

19. The endoscopic device of claim 1, wherein the one or more GUIs present a setup menu comprising a plurality of device setting options.

20. The endoscopic device of claim 19, wherein the plurality of device setting options comprises a system clock setting, a TV out formatting, and a memory card setting.

21. The endoscopic device of claim 1, wherein the one or more GUIs present a return option for returning from a currently displayed GUI to a previously displayed GUI.

22. The endoscopic device of claim 1, wherein the one or more GUIs comprises a home screen that provides a plurality of menu options, the plurality of menu options comprising a new patient option, a viewing option, and a replay option.

23. The endoscopic device of claim 1, wherein the display screen is a touchscreen, and the one or more GUIs present a plurality of user selectable button images.

24. The endoscopic device of claim 1, wherein the handle comprises a plurality of tactile elements in electrical communication with the camera assembly and by which a user can control the camera assembly to acquire the imagery of the uterus.

25. The endoscopic device of claim 1, further comprising an electrical connector configured to relay electrical signals from the camera assembly to the display screen.

26. The endoscopic device of claim 25, further comprising an electrical cable that extends from the camera assembly to the electrical connector.

27. The endoscopic device of claim 1, further comprising a single-use portion that includes the elongate cannula and the camera assembly.

28. The endoscopic device of claim 1, further comprising a multiple-use portion that includes the handle and the display screen.

29. The endoscopic device of claim 1, further comprising one or more of a light emitting diode, a light shield, a light guide, and a prism to facilitate image acquisition by the camera assembly.

30. The endoscopic device of claim 1, wherein the endoscopic device is a hand-held device.

* * * * *

UNITED STATES PATENT AND TRADEMARK OFFICE
CERTIFICATE OF CORRECTION

PATENT NO. : 10,441,134 B2
APPLICATION NO. : 15/868148
DATED : October 15, 2019
INVENTOR(S) : Xiaolong Ouyang et al.

Page 1 of 1

It is certified that error appears in the above-identified patent and that said Letters Patent is hereby corrected as shown below:

In the Claims

Column 20
Line 37, in Claim 14, after "all" delete "of the"

Signed and Sealed this
Seventeenth Day of December, 2019

Andrei Iancu
*Director of the United States Patent and Trademark Office*